(12) United States Patent
Yang et al.

(10) Patent No.: US 12,053,005 B2
(45) Date of Patent: Aug. 6, 2024

(54) **METHOD OF MANUFACTURING TRANSFRUCTOSYLATION STEVIOL GLYCOSIDES USING THE *LACTOBACILLUS MALI***

(71) Applicant: CJ CHEILJEDANG CORPORATION, Seoul (KR)

(72) Inventors: Tae Joo Yang, Seoul (KR); Young Mi Lee, Seoul (KR); In Sung Kang, Seoul (KR); Sunghee Park, Seoul (KR); Young Su Lee, Seoul (KR); Sun Chu, Seoul (KR); Seong Bo Kim, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 713 days.

(21) Appl. No.: 16/768,421

(22) PCT Filed: Dec. 14, 2018

(86) PCT No.: PCT/KR2018/015926
§ 371 (c)(1),
(2) Date: May 29, 2020

(87) PCT Pub. No.: WO2019/117667
PCT Pub. Date: Jun. 20, 2019

(65) Prior Publication Data
US 2020/0383364 A1  Dec. 10, 2020

(30) Foreign Application Priority Data

Dec. 15, 2017  (KR) .................. 10-2017-0173569

(51) Int. Cl.
*C12P 19/56*  (2006.01)
*A23L 27/30*  (2016.01)

(52) U.S. Cl.
CPC ............ *A23L 27/33* (2016.08); *C12P 19/56* (2013.01)

(58) Field of Classification Search
None
See application file for complete search history.

(56) References Cited

U.S. PATENT DOCUMENTS

| 4,219,571 A | 8/1980 | Miyake |
| 2017/0035814 A1 | 2/2017 | Chen et al. |

FOREIGN PATENT DOCUMENTS

| KR | 1995-0002868 B1 | 3/1995 | |
| KR | 10-1199821 B1 | 11/2012 | |
| KR | 10-2013-0014192 A | 2/2013 | |
| KR | 10-2013-0014227 A | 2/2013 | |
| KR | 10-1767606 B1 | 8/2017 | |
| WO | WO 2012 129451 | * 9/2012 | ............... C07H 1/00 |
| WO | 2013/019050 A2 | 2/2013 | |
| WO | 2016/144175 A1 | 9/2016 | |

OTHER PUBLICATIONS

Mathur et al (Int J Pharmacology, 13:916-928, 2017) (Year: 2017).*
Ye et al (LWT Food Science and Technology, 51:524-530, 2013) (Year: 2013).*
Gerwig et al (Carbohydrate Res 440-441:51-62, 2017) (Year: 2017).*
Munoz-Labrado et al (Foods 9:1753, 2020) (Year: 2020).*
Carr et al., "Homofermentative Lactobacilli of Ciders including *Lactobacillus mali* nov. spec." *J. appl. Bact.* 33:768-774 (1970).
Prakash et al., "Development of Next Generation Stevia Sweetener: Rebaudioside M," *Foods* 3:162-175 (2014).
Devlamynck et al., "Glucansucrase Gtf180-ΔN of *Lactobacillus reuteri* 180: enzyme and reaction engineering for improved glycosylation of non-carbohydrate molecules," *Appl Microbiol Biotechnol* 100:7529-7539 (2016).
Gerwig et al., "Structural analysis of rebaudioside A derivatives obtained by *Lactobacillus reuteri* 180 glucansucrase-catalyzed trans-α-glucosylation," *Carbohydrate Research* 440-441:51-62 (2017).
Seto et al., "Effective cellulose production by a coculture of *Gluconacetobacter xylinus* and *Lactobacillus mali*," *Appl Microbiol Biotechnol* 73:915-921 (2006).

* cited by examiner

*Primary Examiner* — Craig D Ricci
(74) *Attorney, Agent, or Firm* — Seed IP Law Group LLP

(57) ABSTRACT

The present disclosure relates to a method for preparing a transglucosylated steviol glycoside using a crude enzyme liquid of a *Lactobacillus mali* strain.

4 Claims, 18 Drawing Sheets

[Fig. 1]
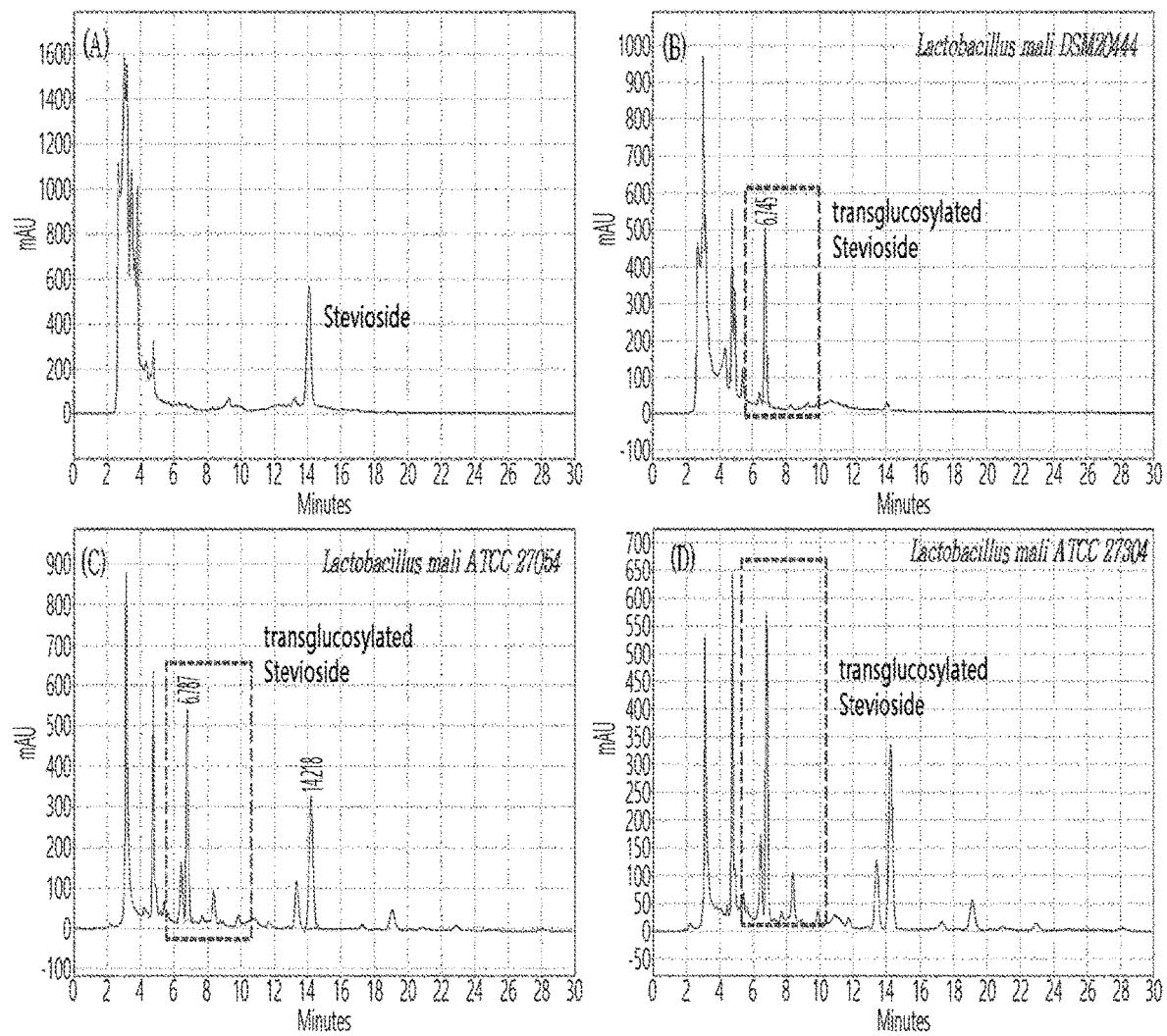

[Fig. 2]
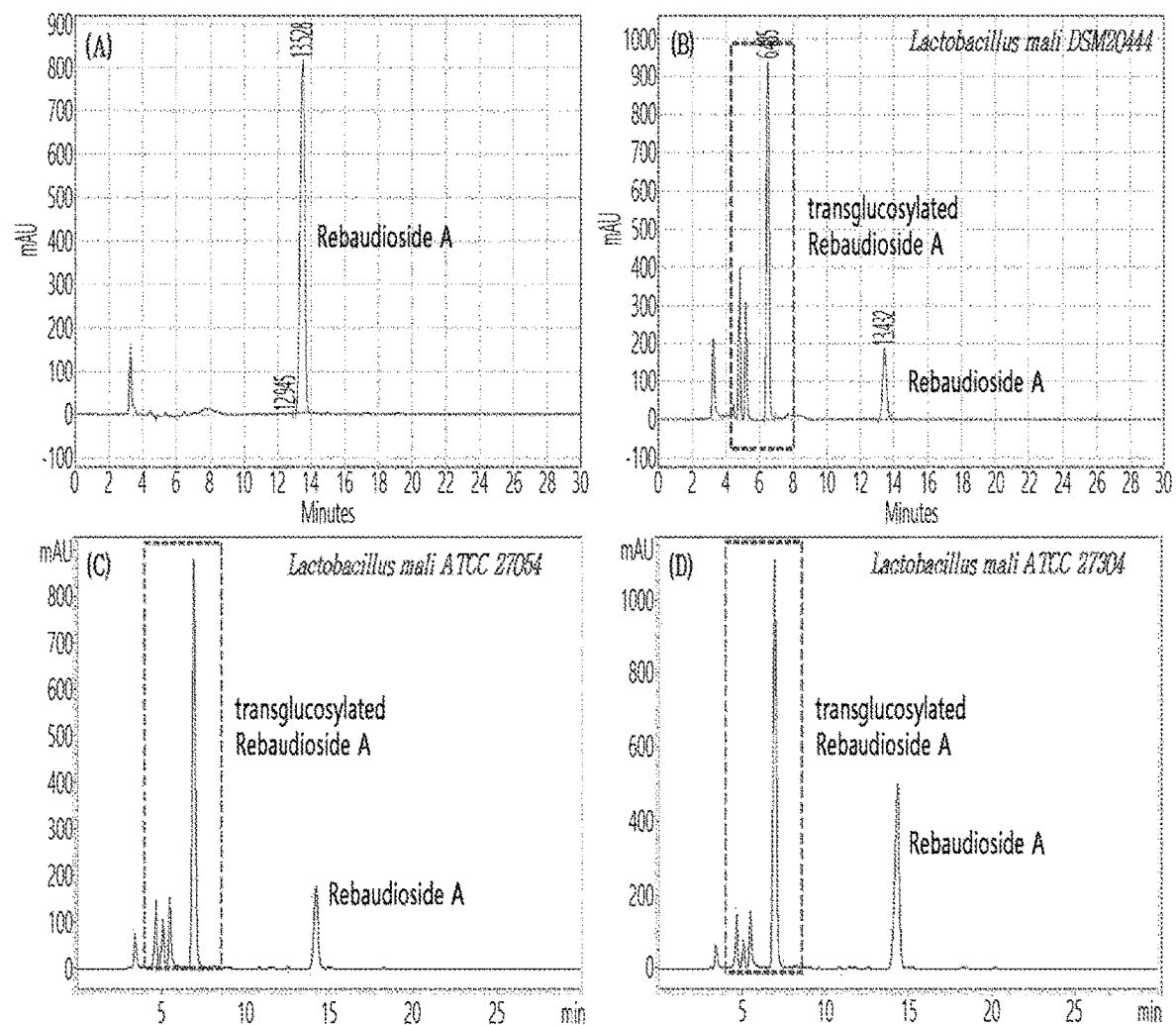

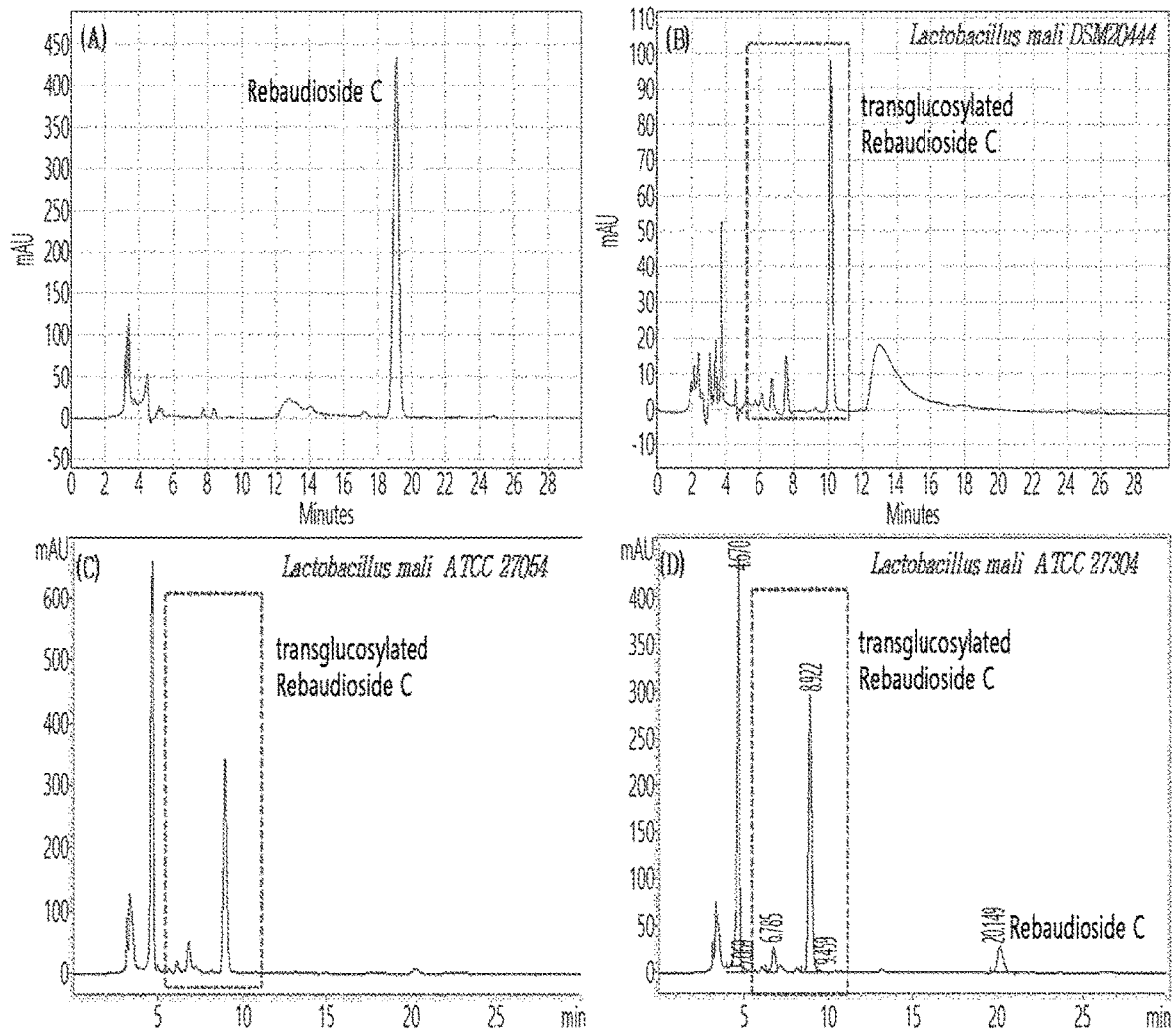
[Fig. 3]

[Fig. 4]
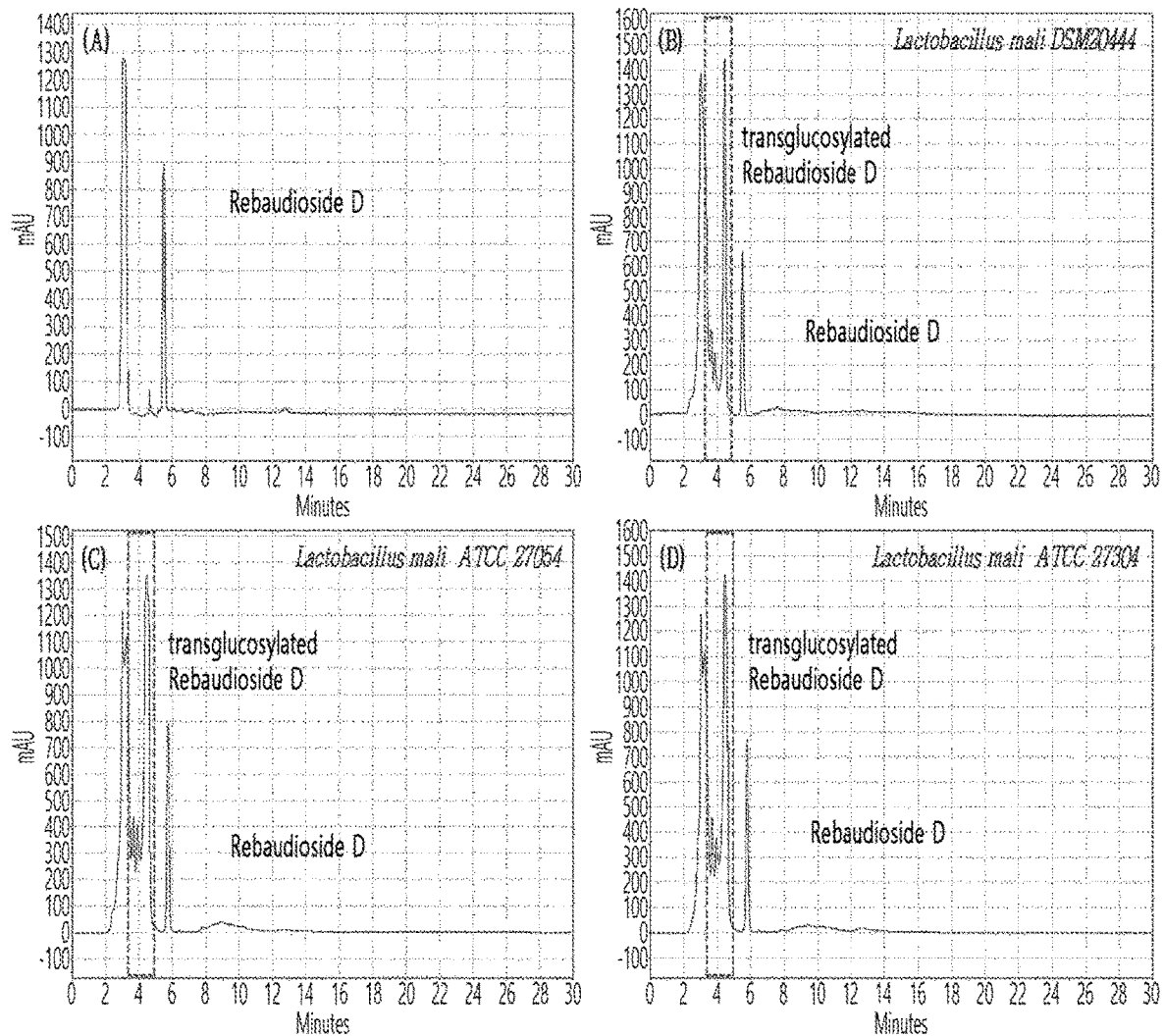

[Fig. 5]
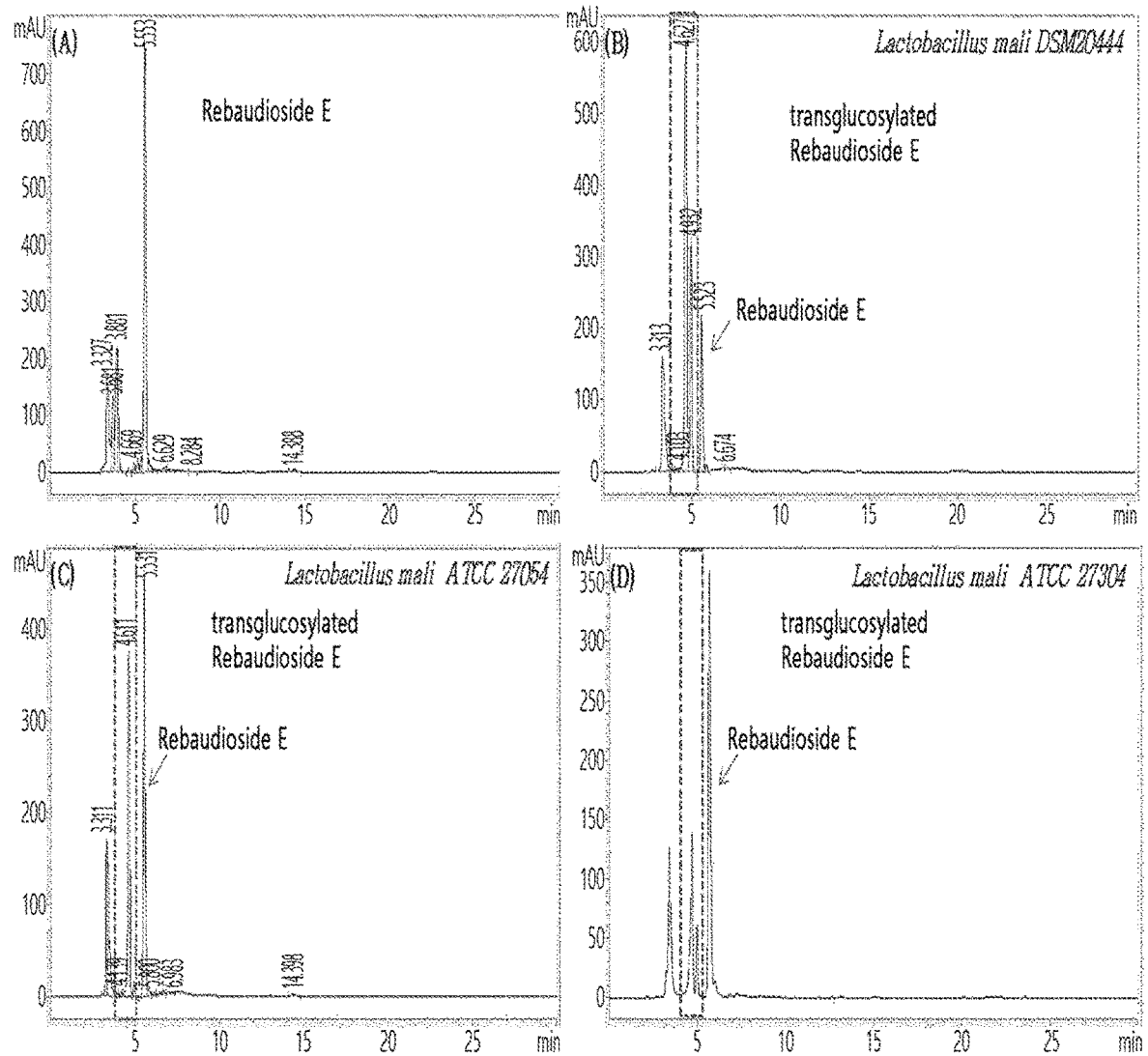

[Fig. 6]
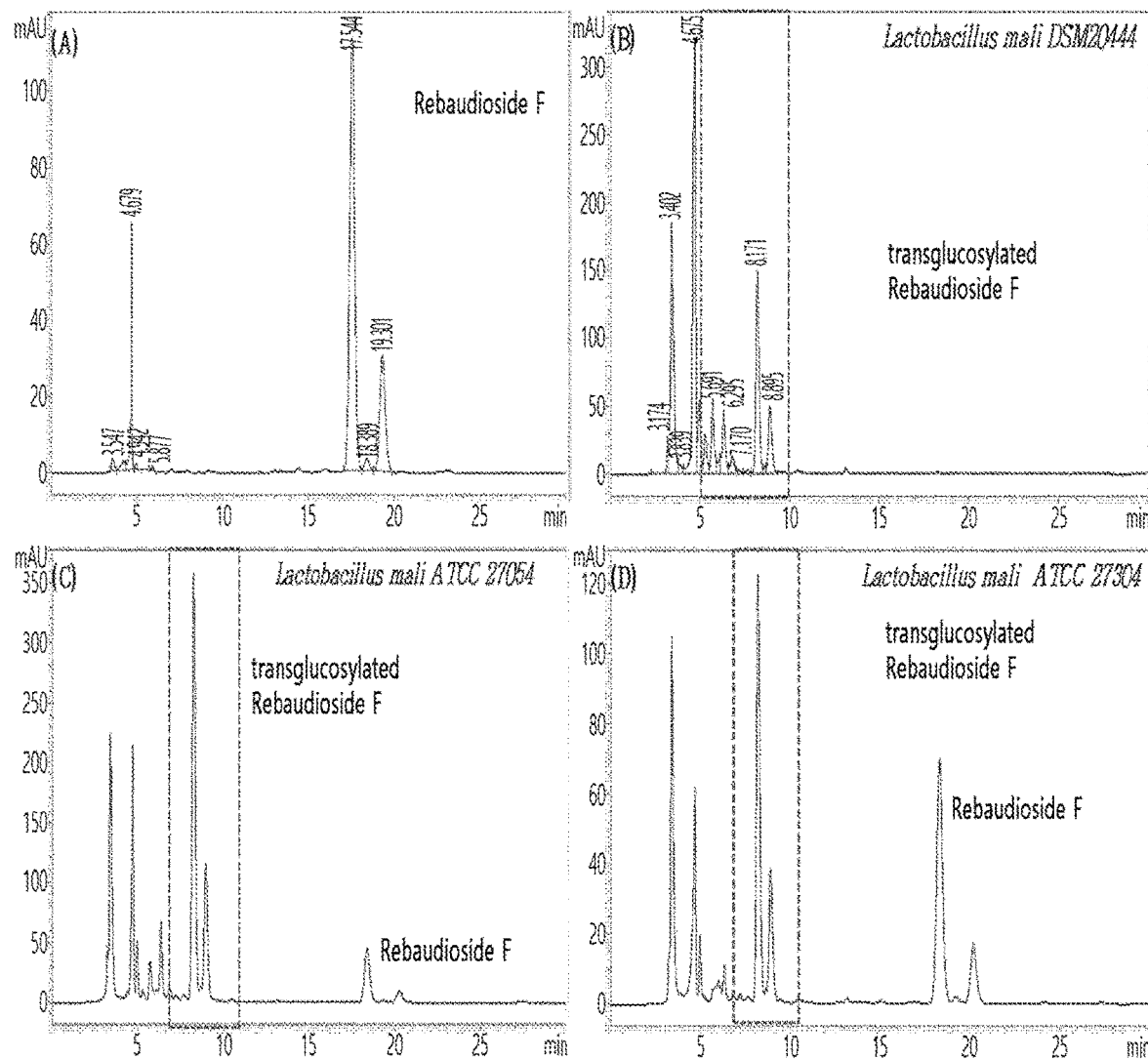

[Fig. 7]
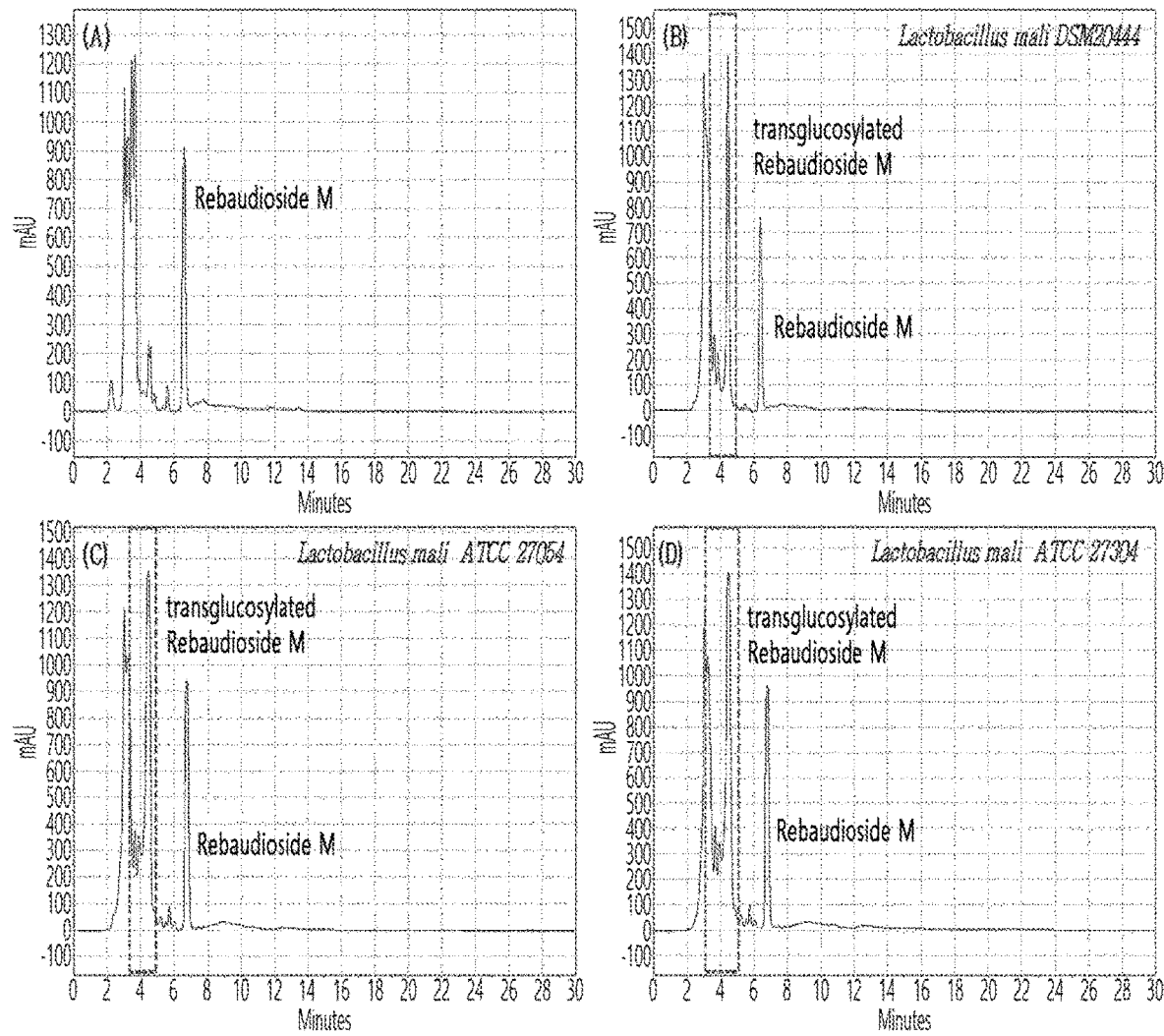

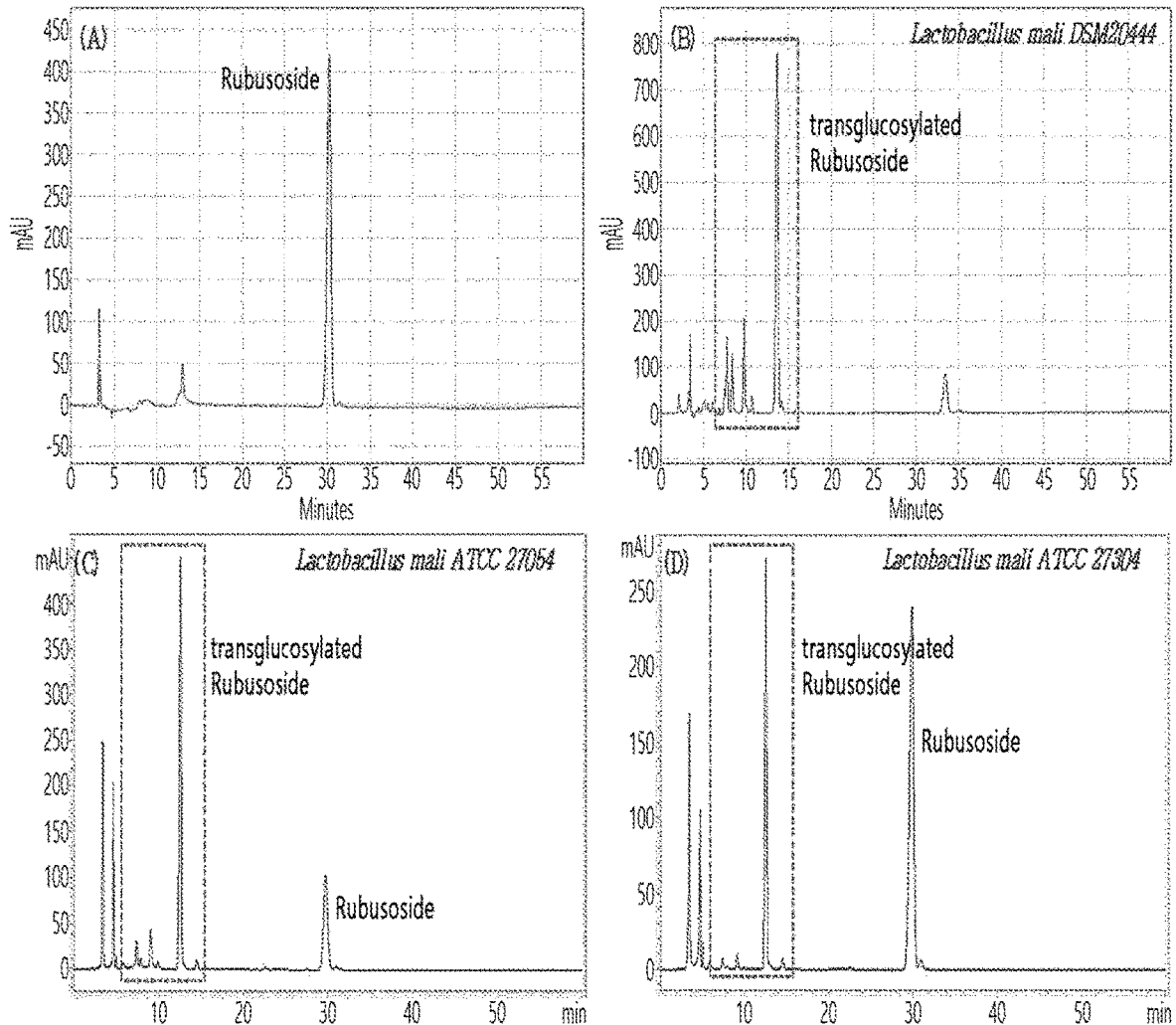
[Fig. 8]

[Fig. 9]
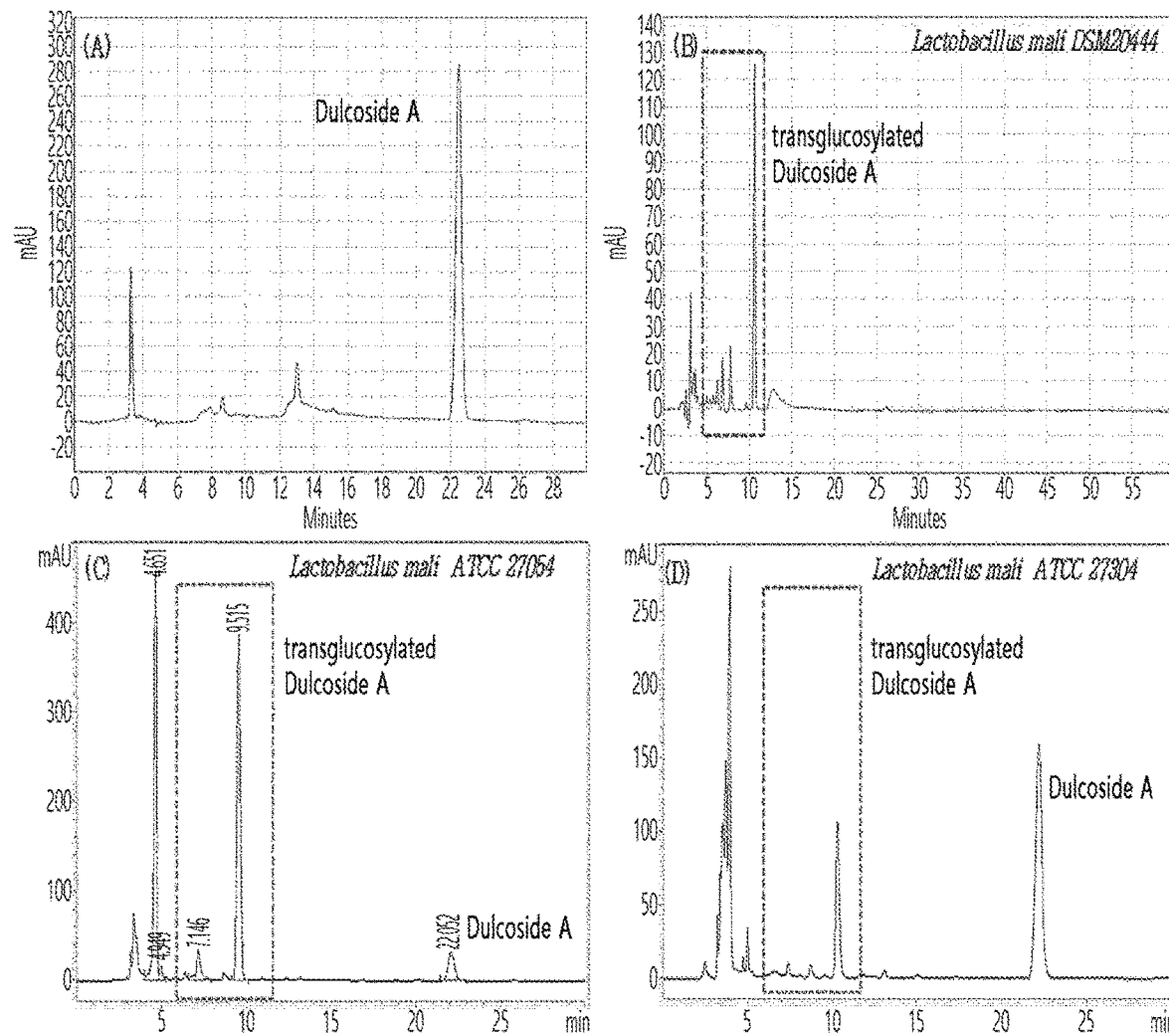

[Fig. 10]
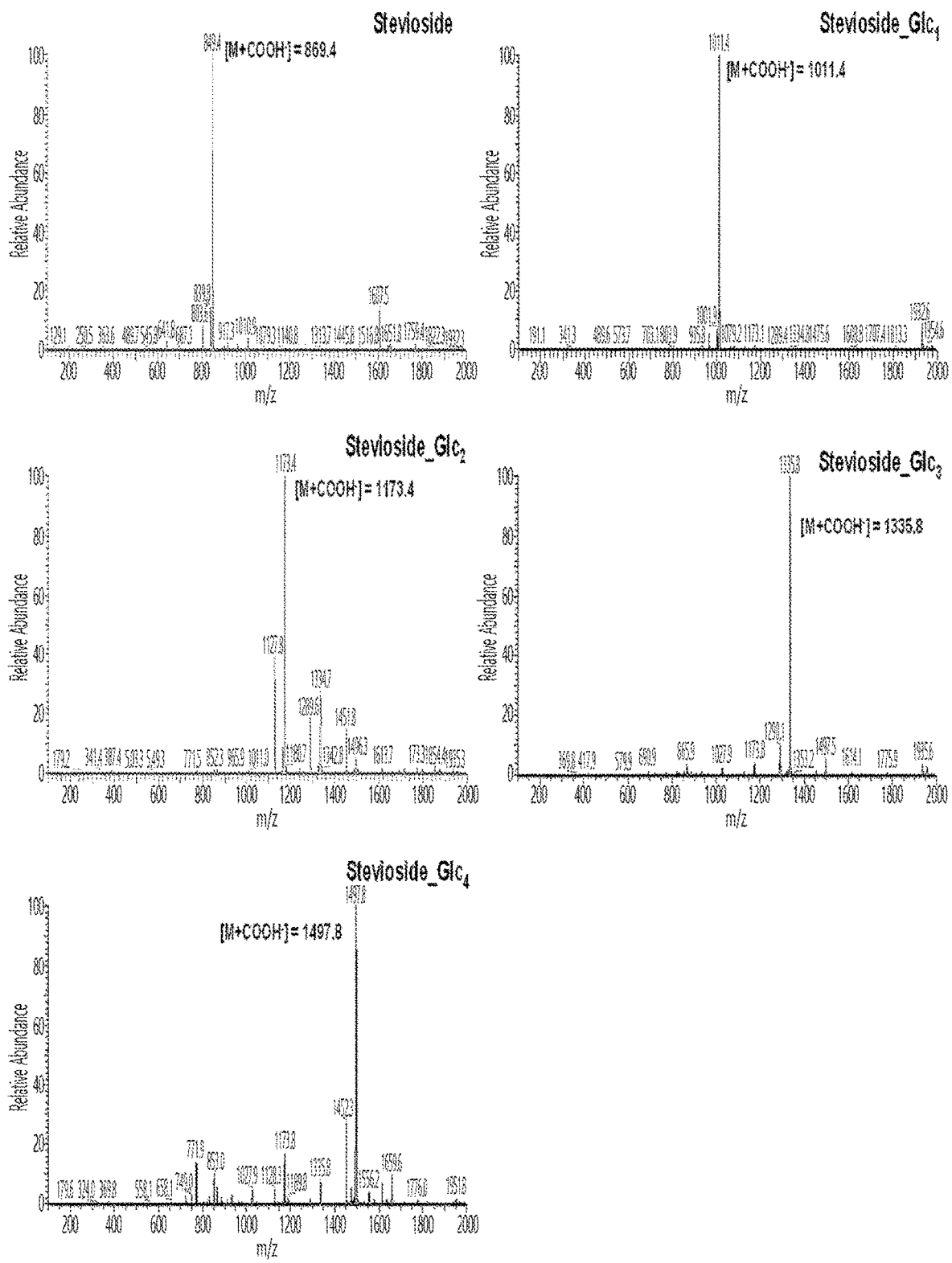

[Fig. 11]
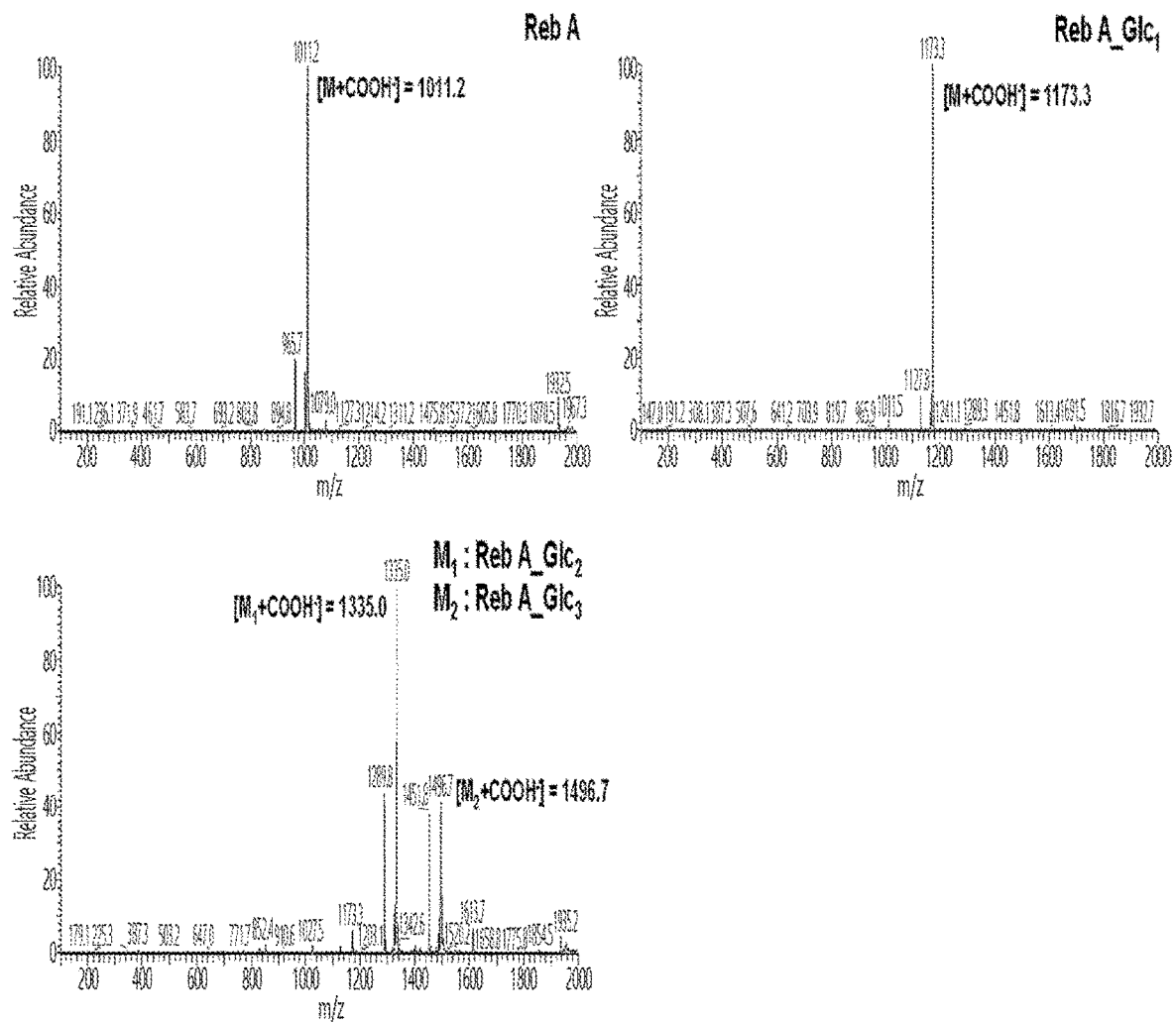

[Fig. 12]
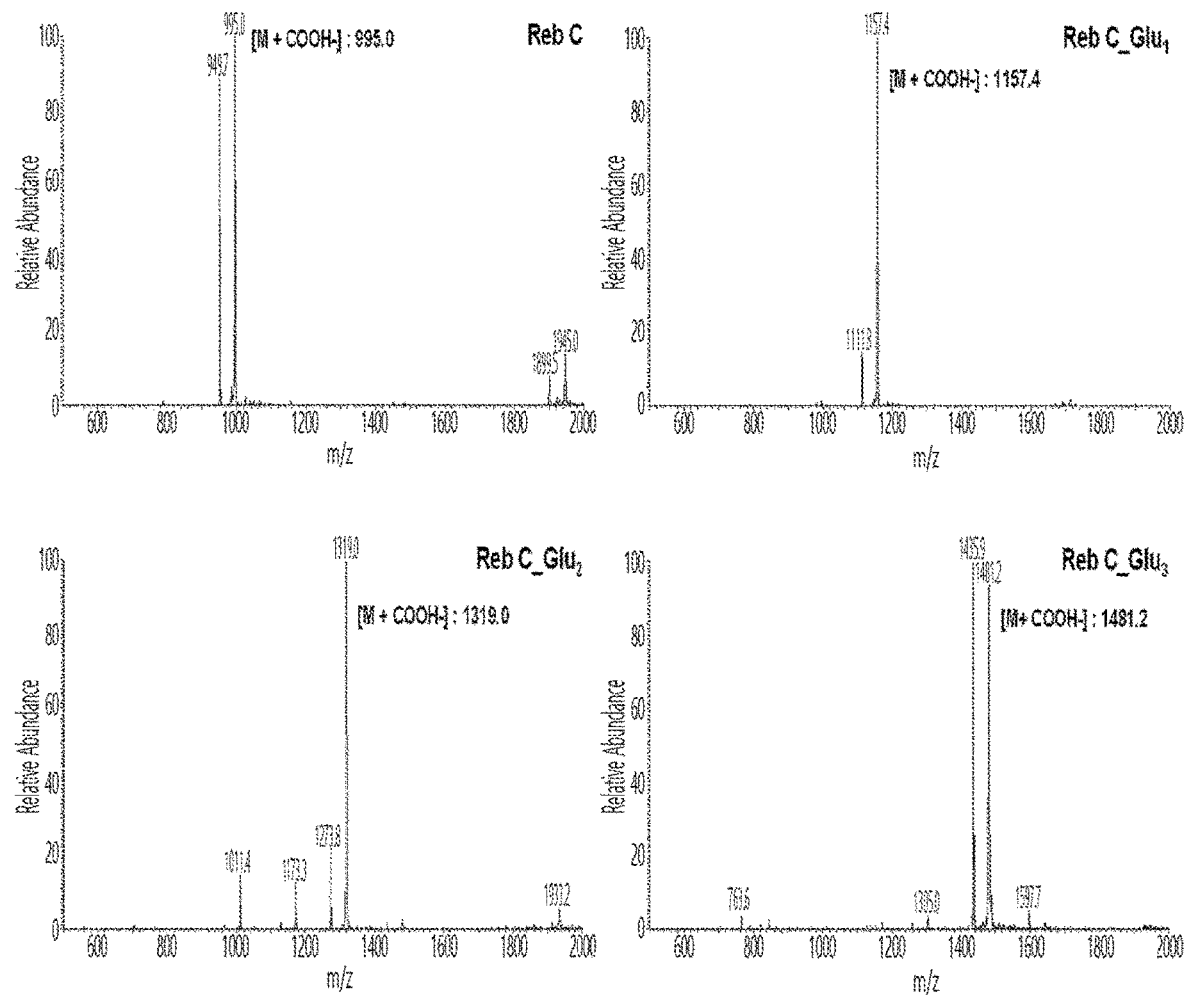

[Fig. 13]
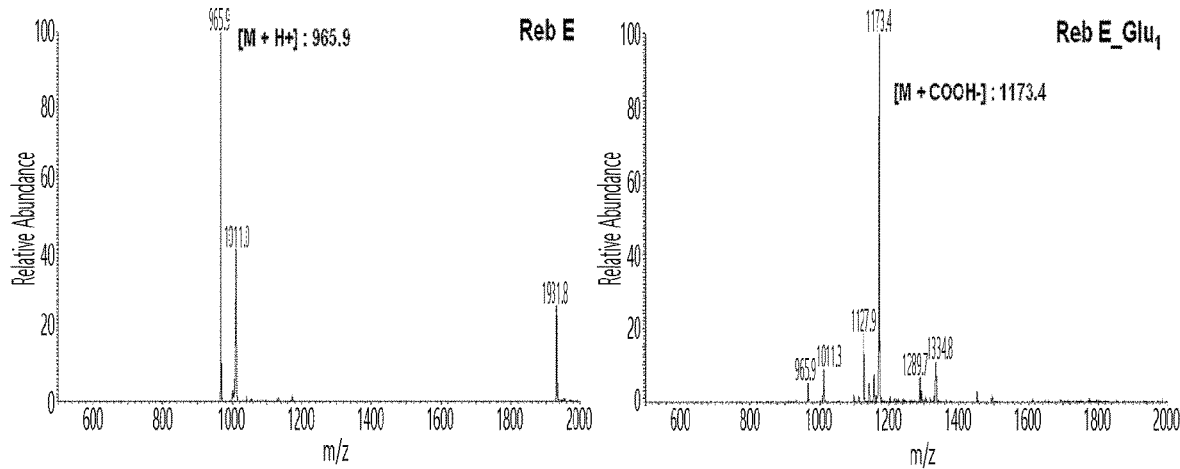
[Fig. 14]
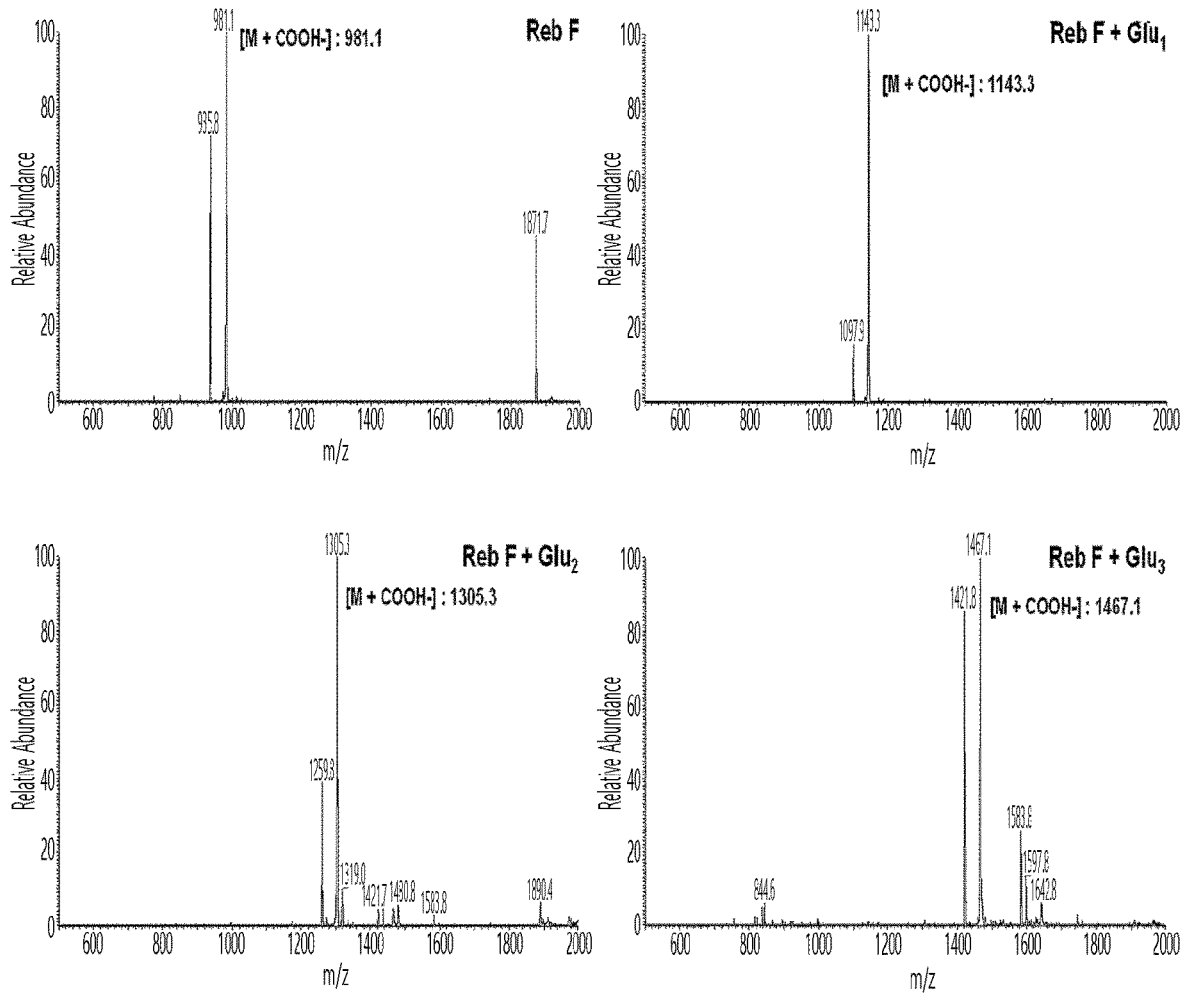

[Fig. 15]
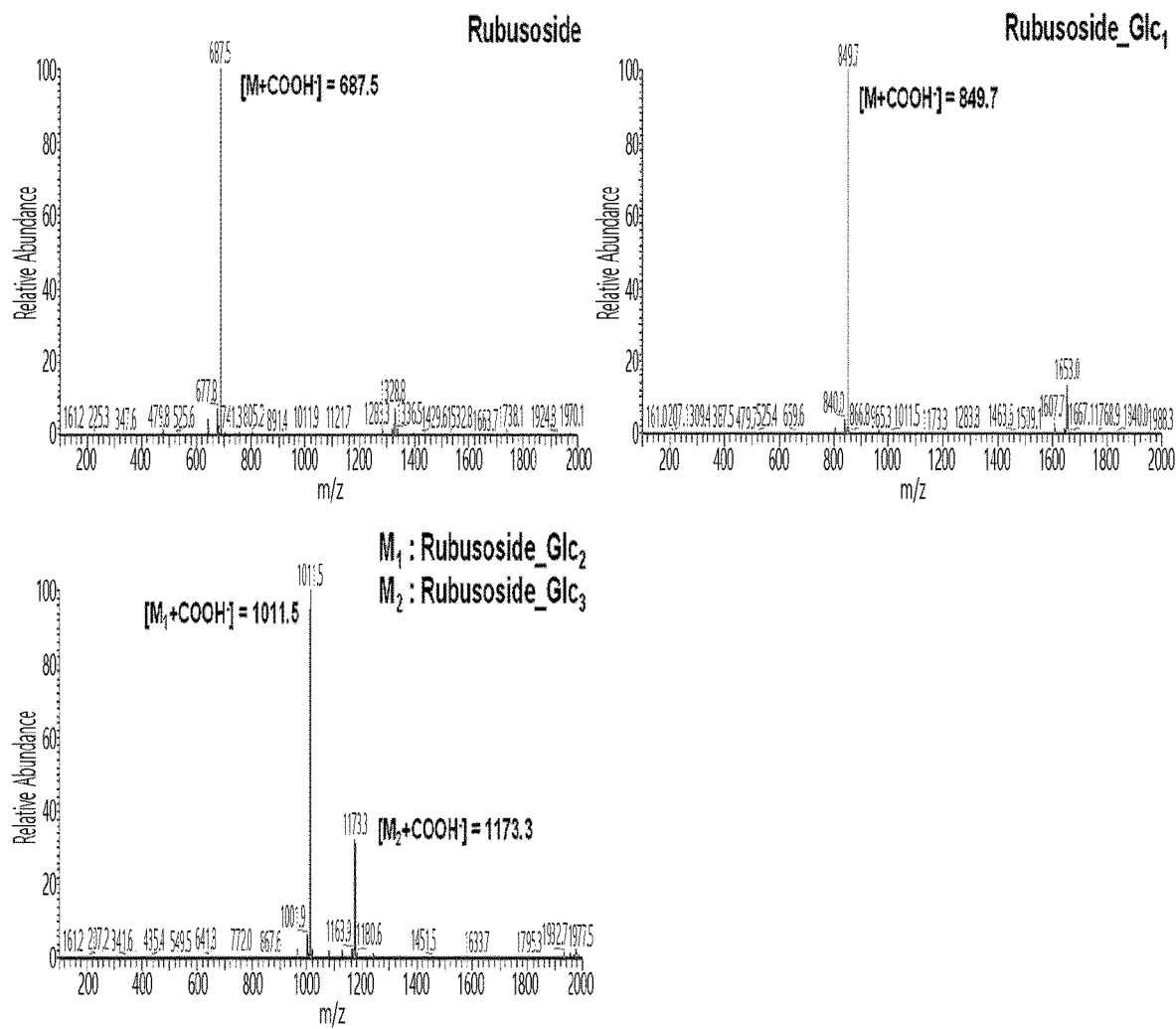

[Fig. 16]
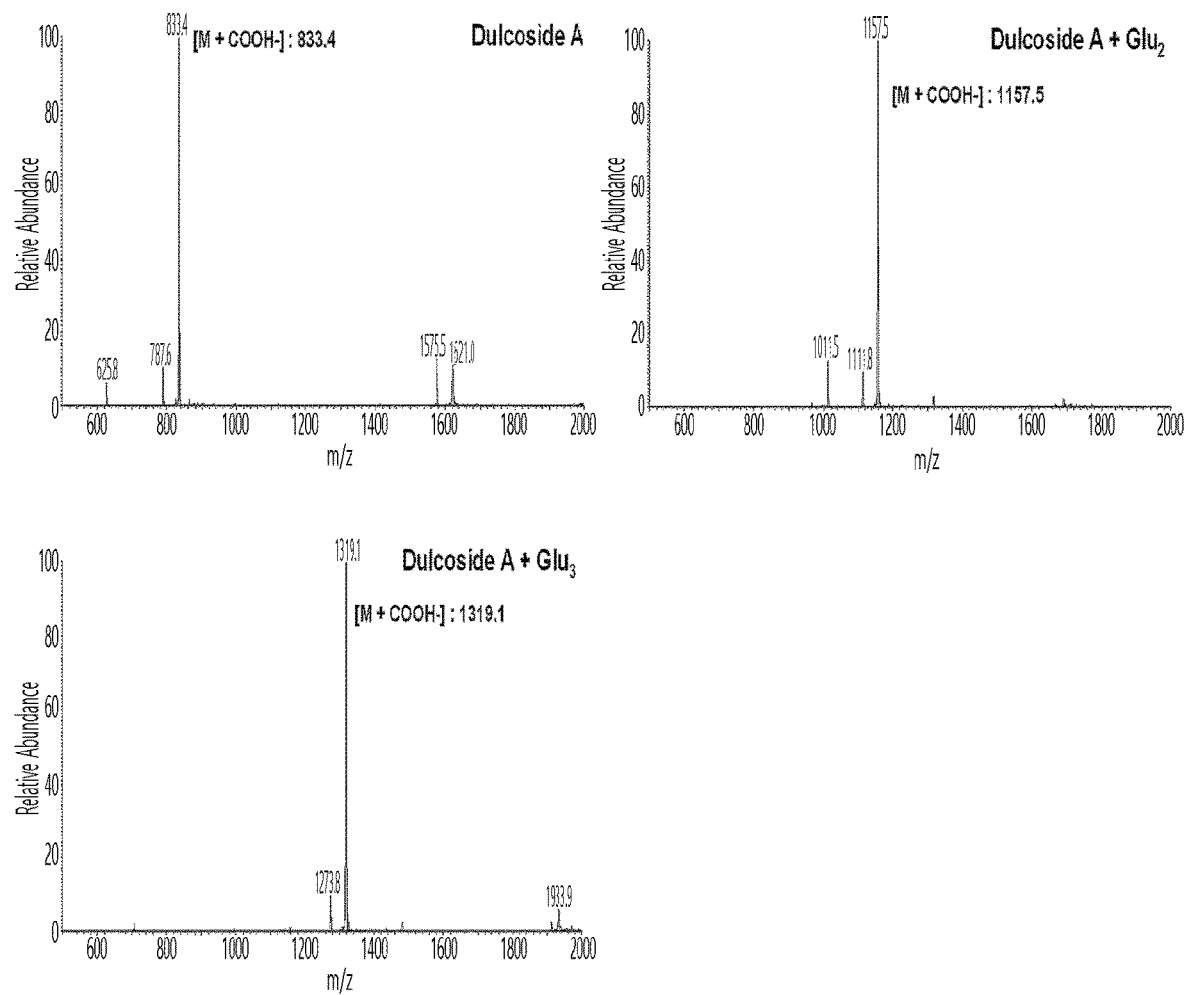

[Fig. 17]
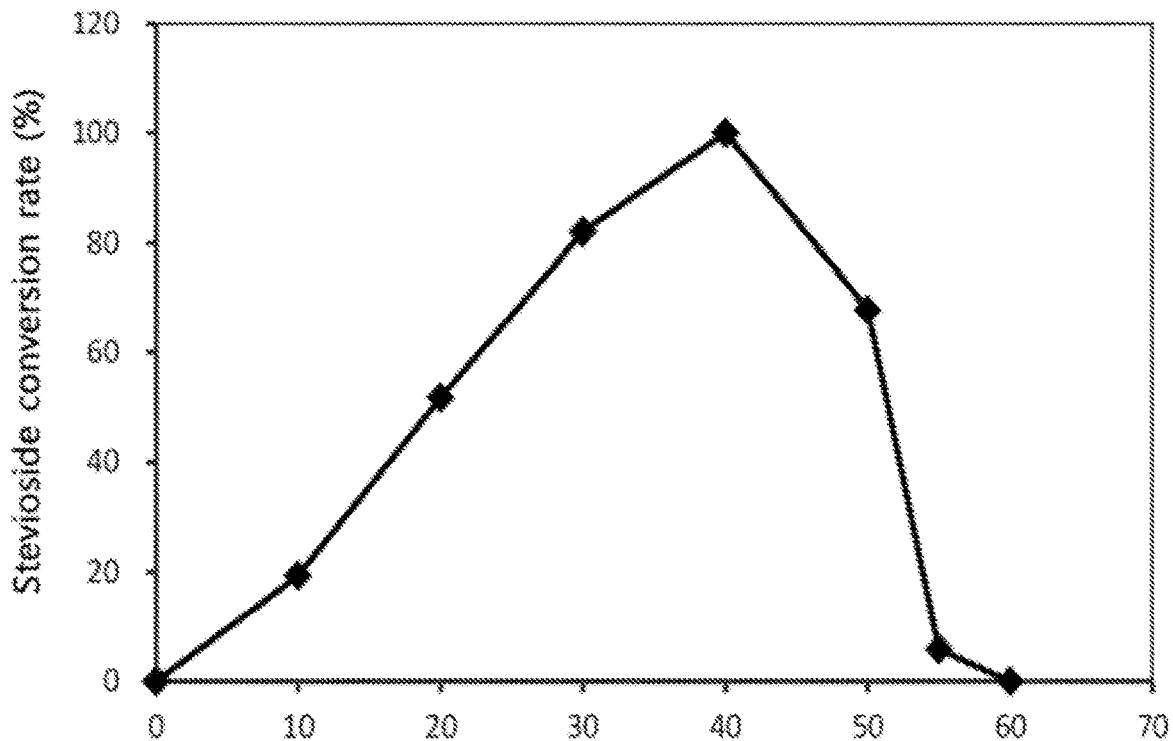
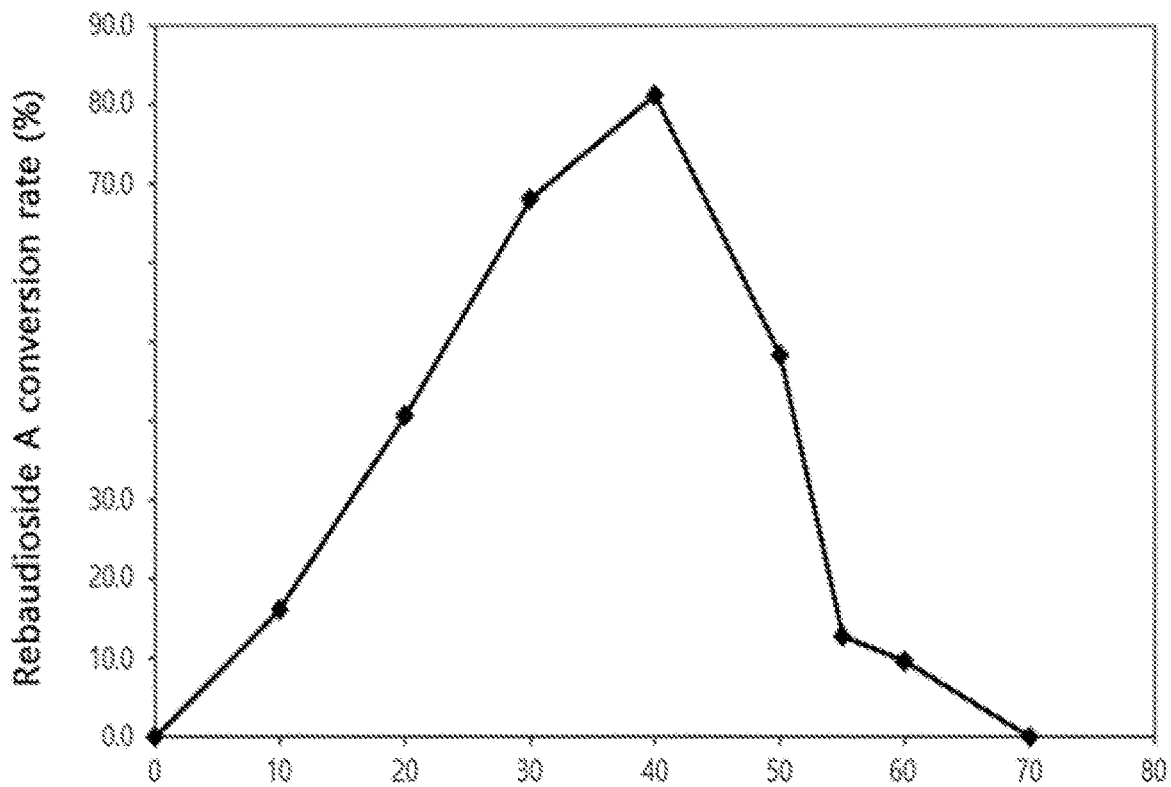

[Fig. 18]
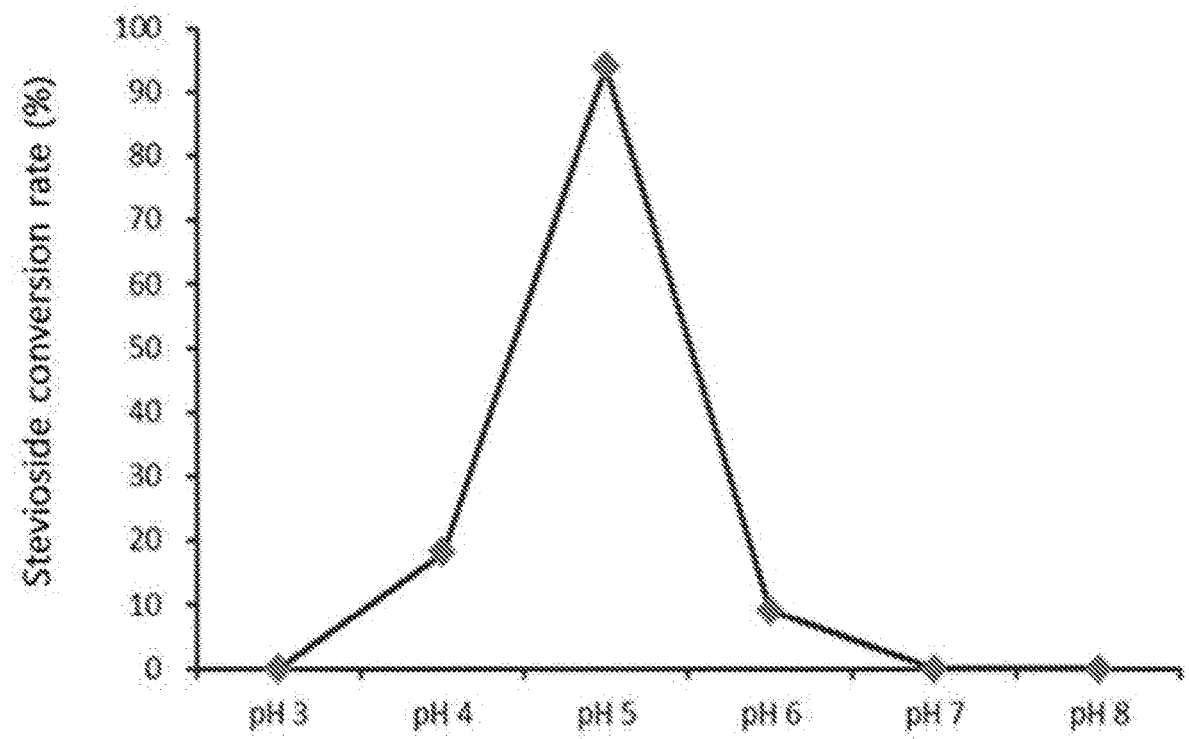
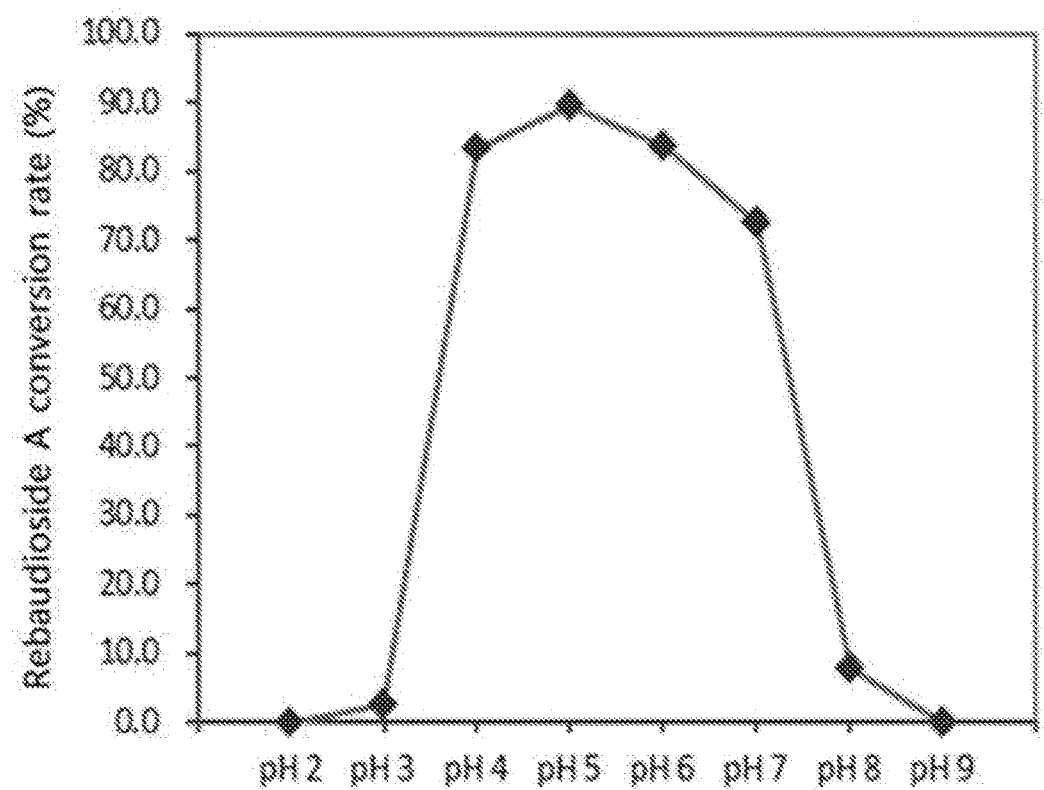

[Fig. 19]
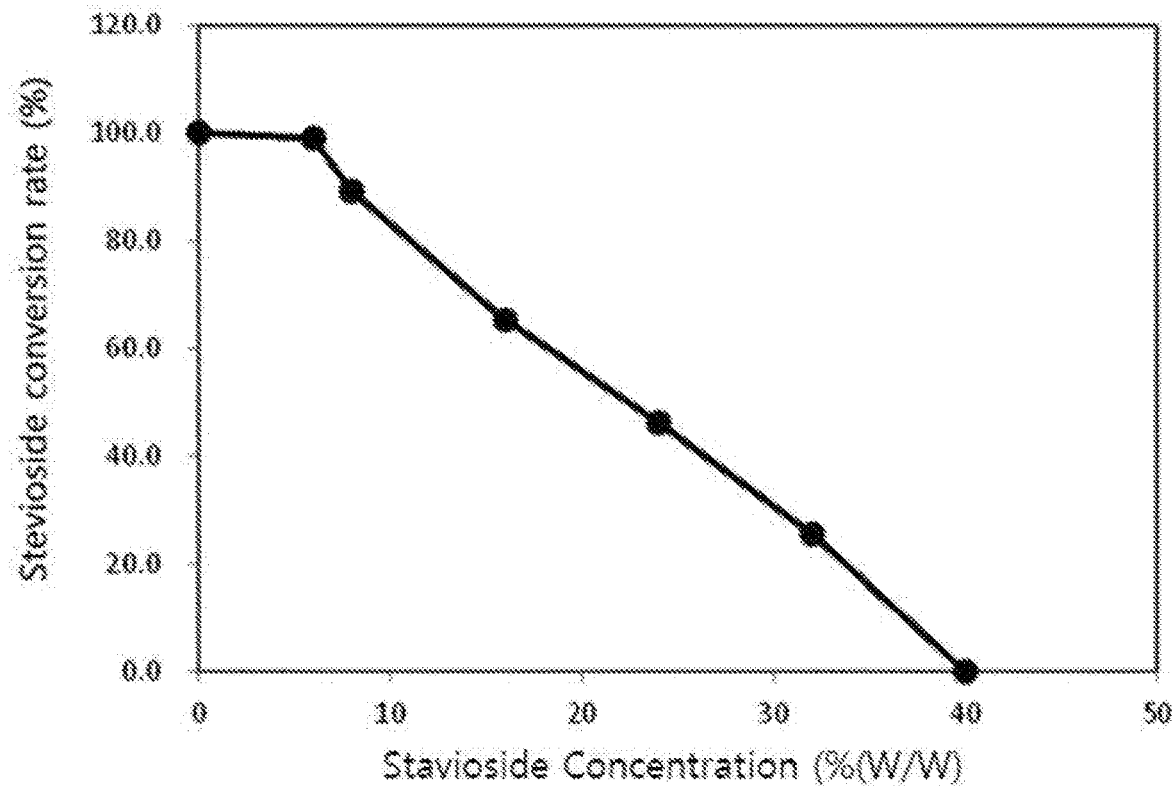
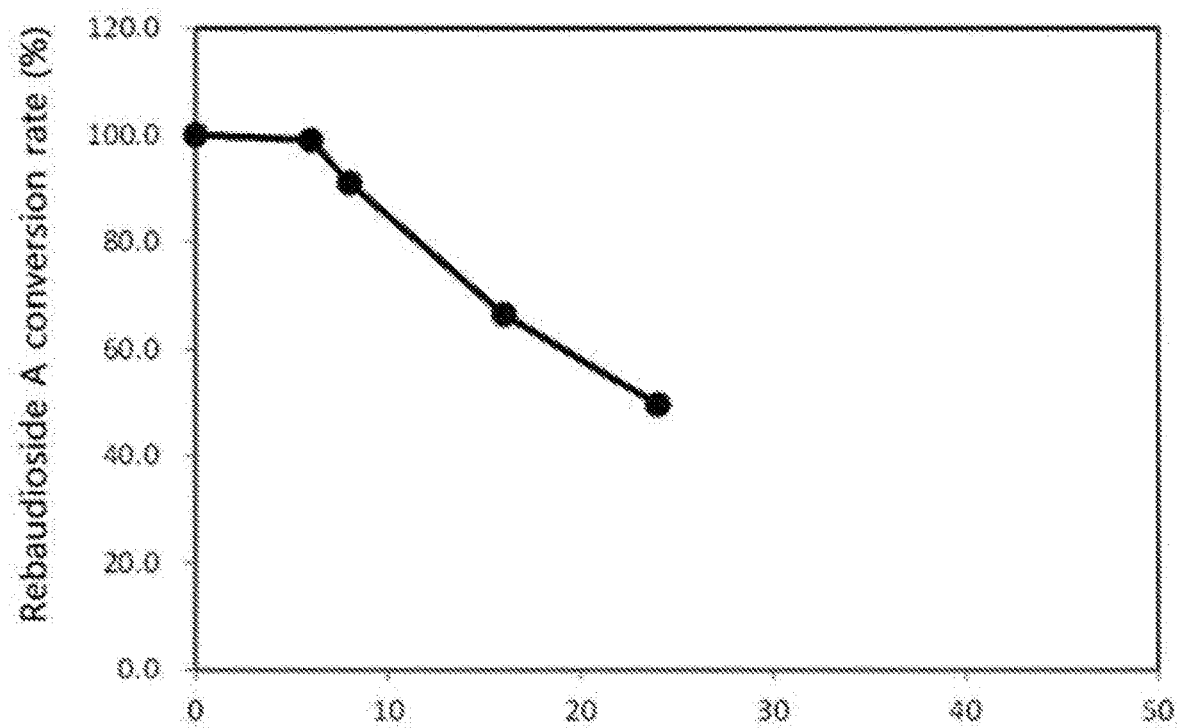

METHOD OF MANUFACTURING TRANSFRUCTOSYLATION STEVIOL GLYCOSIDES USING THE *LACTOBACILLUS MALI*

TECHNICAL FIELD

The present disclosure relates to a method for preparing a transglucosylated steviol glycoside using a crude enzyme liquid of a *Lactobacillus mali* strain.

BACKGROUND ART

As the World Health Organization (WHO) recommends lowering the amount of daily sugar intake due to concerns about disease (obesity) caused by sugar consumption, various policies aimed at reducing the amount of sugar intake are actively being discussed by the governments of developed countries. Therefore, as the need for developing various alternative sweeteners is increasing in the market, alternative sweeteners are continuously being developed and commercialized. As alternative sweeteners, these are the subject of continuous variation in the form of synthetic high-intensity sweeteners (e.g., Saccharin, Aspartame, Sucralose, etc.), synthetic sugar alcohols (e.g., Maltitol and Xylitol), and high-intensity sweeteners (e.g., Rebaudioside A and Liquorice). Nevertheless, due to concerns over the safety of synthetic sweeteners, customers' need for natural sweeteners has been steadily increasing; however, because of limitations to peculiar flavor properties of natural sweeteners (i.e., off-oder and off-flavor), natural sweeteners cannot fully replace existing low-calorie and zero-calorie products based on synthetic sweeteners.

A natural high-intensity sweetener that has received considerable attention in recent years is *stevia* extracted from the leaves of *Stevia rebaudiana Berloni*. *Stevia* is a natural material, the sweetness of which is 200 to 300 times that of sugar. Further, *stevia* consists of Stevioside, Rebaudioside A, B, C, D, E, and M, etc. Furthermore, *stevia* has a potential use as an alternative sweetener because it has been reported that it does not generate calories, it is positive for blood glucose and insulin levels, and it has no side effects on the human body; however, *stevia* has a bitter taste, which presents a limitation in use.

Thus far, there have been three methods to improve the sweetness of *stevia*: (1) a method of mixing with a saccharide sweetener, an amino acid, or an amino acid salt, (2) a physical method of including a material such as cyclodextrin; and (3) a method of transferring glucose using an enzyme. As the method of transferring glucose using an enzyme, a method of transferring 1 to 12 glucose molecules to a steviol glycoside using CGTase is widely used in the art (Korean Patent Application No. 10-1991-0020769). However, such method has a disadvantage in that all glucose transferred to the steviol glycoside is degraded by intestinal microorganisms, increasing calories.

General lactobacilli are known to produce rubusoside when reacted with β-glucosidase (Korean Patent Application No. 10-17676060000). In addition, a particular genome *Lactobacillus reuteri* 180 is the only *lactobacillus* known to recognize a steviol glycoside to produce a transglucosylated steviol glycoside.

Under such circumstances, the present inventors have completed the present disclosure by discovering that the *Lactobacillus mali* transglucosylate glucose to a steviol glycoside by a α-(1,6)-bond to produce an indigestible transglucosylated steviol glycoside.

DISCLOSURE

Technical Problem

An object of the present disclosure is to provide a method for preparing a transglucosylated steviol glycoside using a *Lactobacillus mali* microorganism or a culture thereof.

Another object of the present disclosure is to provide a transglucosylated steviol glycoside prepared via the preparation method above.

Still another object of the present disclosure is to provide a composition for producing the transglucosylated steviol glycoside, comprising a *Lactobacillus mali* microorganism or a culture thereof.

Still another object of the present disclosure is to provide a sweetener comprising transglucosylated steviol glycoside prepared via the preparation method above using the *Lactobacillus mali* microorganism or culture thereof.

Technical Solution

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the objects of the present disclosure, an aspect of the present disclosure provides a method for preparing a transglucosylated steviol glycoside using a *Lactobacillus mali* microorganism or a culture thereof.

As used herein, the term "steviol glycoside" refers to a natural sweetener having a glucose, rhamnose, xylose, etc. linked to a 13-OH or 19-OH of Chemical Formula 1:

[Chemical Formula 1]

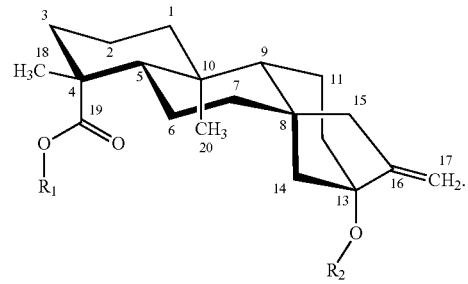

Generally, in Chemical Formula 1, at $R_1$, hydrogen (H) may be bound, or 1 to 3 glucose molecules may be bound via a β-bond; and at $R_2$, any one of glucose, xylose, and rhamnose may be bound, and 0 to 2 glucose molecules may be bound thereto via a β-bond, but these are not limited thereto.

The steviol glycoside is advantageous in that it has fewer calories compared with sugar, and that the sweetness thereof is about 200 to 300 times that of sugar; but is disadvantageous in that it is accompanied by a unique astringent or bitter taste. Therefore, efforts have been made to improve the sweetness of the steviol glycoside.

The α-/β-glycosidic bonds are distinguished by the anomeric position and relative stereochemistry (R-type or S-type) of the stereocenter which is the most distant from the 1-carbon of a monosaccharide. In general, the α-glycosidic bond is formed when two carbons have the same stereochemistry, whereas the β-glycosidic bond occurs when two carbons have different stereochemistry.

The present inventors have found for the first time that a *Lactobacillus mali* microorganism and a culture thereof decompose sugar into glucose using the sugar and steviol glycoside as a substrate, and selectively link 1 to 4 glucose molecules to the steviol glycoside by an α-bond. In addition, the present inventors have first discovered that enzymes derived from the *Lactobacillus mali* of the present disclosure are advantageous in that they have an excellent conversion rate into a transglucosylated steviol glycoside, and that the odor thereof is decreased and the sweetness thereof is remarkably increased compared to an existing steviol glycoside.

As used herein, the term "transglucosylated steviol glycoside" may refer to a steviol glycoside having the form in which, by using sugar and a steviol glycoside as substrates, 1 to 4 glucose molecules are added directly to a 19-OH site of the steviol glycoside via an α-bond by the *Lactobacillus mali*. More specifically, the transglucosylated steviol glycoside may be in the form wherein 1 to 4 glucose molecules are added to a glucose linked to the 19-OH site of the steviol glycoside by an α-(1,6) bond, but is not limited thereto.

Each step of the method for preparing the transglucosylated steviol glycoside will be described in detail. First, in the method, a *Lactobacillus mali* microorganism or a culture thereof may be prepared.

In the next step of the method for preparing the transglucosylated steviol glycoside, sugar may be reacted with a steviol glycoside in the presence of the *Lactobacillus mali* microorganism or a culture thereof.

For the purpose of the present disclosure, the culture may refer to a culture medium containing cells or crude enzyme liquid excluding the cells. The enzyme having sugar hydrolytic activity may play a role of selectively α-binding 1 to 4 glucose molecules to the glucose linked to the 19-OH site of the steviol glycoside, but is not limited thereto.

Herein, the steviol glycoside may be one or more selected from the group consisting of Stevioside, Rubusoside, Dulcoside A, Rebaudioside A, Rebaudioside C, Rebaudioside D, Rebaudioside E, Rebaudioside F, and Rebaudioside M, but is not limited thereto.

Further, the step of contacting sugar with the steviol glycoside may be carried out at a pH of 1 to 10, more specifically at a pH of 2 to 9, or at a pH of 3 to 8, but the pH is not limited thereto.

Additionally, the step of contacting sugar with the steviol glycoside may be carried out at a temperature of 1° C. to 80° C., more specifically at a temperature of 5° C. to 70° C., 10° C. to 60° C., or 25° C. to 50° C., but the temperature is not limited thereto.

In addition, the *Lactobacillus mali* having a characteristic of transglucosylated steviol glycoside features in having a higher conversion rate from the steviol glycoside into a transglucosylated steviol glycoside compared to other microorganisms containing known enzymes.

The conversion rate into the transglucosylated steviol glycoside of the present disclosure may be 40% to 90%, but is not limited thereto. More specifically, the conversion rate may be 40% to 90%, 50% to 80%, 50% to 85%, 60% to 85%, 60% to 80%, 70% to 85%, or 70% to 80%, but is not limited thereto More specifically, the conversion rate was measured under the condition in which a culture medium in which the *Lactobacillus mali* having a characteristic of transglucosylated steviol glycoside is cultured at 30° C. for 24 hours to 48 hours is centrifuged at 4000 rpm to 8000 rpm for 1 minute to 20 minutes to separate the cells and react the crude enzyme liquid with the substrate solution containing the steviol glycosylated and sugar.

In order to achieve the objects of the present disclosure, another aspect of the present disclosure provides a transglucosylated steviol glycoside prepared by the preparation method above. The transglucosylated steviol glycoside may be in the form in which 1 to 4 glucose molecules are added directly to a 19-OH site of the steviol glycoside via an α-bond, and more specifically may be in the form in which 1 to 4 glucose molecules are added directly to a 19-OH site of the steviol glycoside via an α-(1,6) bond, but is not limited thereto.

More specifically, the transglucosylated steviol glycoside prepared according to the method above may be one or more selected from the group consisting of transglucosylated Stevioside, transglucosylated Rubusoside, transglucosylated Dulcoside A, transglucosylated Rebaudioside A, transglucosylated Rebaudioside C, transglucosylated Rebaudioside D, transglucosylated Rebaudioside E, transglucosylated Rebaudioside F, and transglucosylated Rebaudioside M, but is not limited thereto.

Still another aspect of the present disclosure provides a composition for producing the transglucosylated steviol glycoside, comprising a *Lactobacillus mali* microorganism or a culture thereof.

Still another aspect of the present disclosure provides a sweetener comprising transglucosylated steviol glycoside prepared via the method. For the purpose of the present disclosure, the sweetener is characterized in having reduced off-odors and enhanced sweetness.

Still another aspect of the present disclosure provides a method for enhancing sweetness of the sweetener comprising producing a transglucosylated steviol glycoside using a *Lactobacillus mali* microorganism or a culture thereof.

Advantageous Effects

The method of the present disclosure for preparing a transglucosylated steviol glycoside can specifically produce a transglucosylated steviol glycoside using a *Lactobacillus mali* microorganism or a culture thereof. In addition, the transglucosylated steviol glycoside has a high conversion rate from the steviol glycoside into a transglucosylated steviol glycoside, and thus can effectively produce transglucosylated steviol glycosides. The transglucosylated steviol glycoside according to the present disclosure is a material for a high-intensity sweetener having an improved bitter taste and of which the caloric content is not high compared to a known transglucosylated steviol glycoside, and can thereby be used in various fields.

BRIEF DESCRIPTION OF DRAWINGS

FIGS. 1 to 9 show HPLC results of the transglucosylated steviol glycosides prepared using the crude enzyme liquid of the *Lactobacillus mali* strain.

FIGS. 10 to 16 show HPLC/MS results of the transglucosylated steviol glycosides prepared using the crude enzyme liquid of the *Lactobacillus mali* strain.

FIG. 17 is graphs showing the conversion rate of the transglucosylated steviol glycosides (Stevioside and Rebaudioside A) according to temperature.

FIG. 18 is graphs showing the conversion rate of the transglucosylated steviol glycosides (Stevioside and Rebaudioside A) according to pH.

FIG. 19 is graphs showing the conversion rate of the transglucosylated steviol glycoside according to concentrations of the steviol glycosides (Stevioside and Rebaudioside A).

DETAILED DESCRIPTION OF THE INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Preparation Method of a Novel Lactobacillus mali-Derived Enzyme Having Sugar Hydrolytic Activity In a nutrient medium containing a yeast extract and corn steep liquor as nitrogen sources and sugar (Beksul white sugar having a purity of 99% or higher) as a carbon source, amino acids, etc., Lactobacillus mali microorganisms (DSM20444, ATCC 27054, ATCC 27304) were individually cultured for 24 hours at 30° C. The culture media (cultures) were centrifuged at 8000 rpm for 10 minutes to separate the cells and supernatants, and then the supernatants were only collected. The crude enzyme liquid was reacted with sugar, which led to sugar hydrolytic activity, and this confirmed the presence of the novel enzyme having sugar hydrolytic activity in the crude enzyme liquid.

Example 2: Evaluation of Conversion from Steviol Glycoside into Transglucosylated Steviol Glycoside Steviol glycosides and sugar were dissolved in a 0.05 M acetate buffer solution, and the crude enzyme liquids of the crude enzyme liquid of the Lactobacillus mali strain, which had been prepared in Example 1, were added thereto, followed by contacting at 40° C. for 24 hours. After the reaction, the reaction solutions were inactivated at 100° C., and then the production of transglucosylated steviol glycosides was confirmed by HPLC. The steviol glycosides used are Stevioside, Rubusoside, Dulcoside A, and Rebaudiosides A/C/D/E/F/M, and whether they produced transgucosylated Stevioside, transglucosylated Rubusoside, transglucosylated Dulcoside A, and transglucosylated Rebaudiosides A/C/D/E/F/M was determined by HPLC. Specifically, the molecular weights of the transglucosylated steviol glycosides were determined by carrying out HPLC/MS analysis based on FIGS. 1 to 9 to identify the substances newly produced by the reaction between the crude enzyme liquid of the Lactobacillus mali strain and the steviol glycoside, and the substances were confirmed to be transglucosylated steviol glycosides. The HPLC/MS analysis-conducted steviol glycosides are stevioside, Rebaudiosides A/C/D/E/F/M, Rubusoside, and Ducoside A.

FIGS. 10 to 16 show the results of the HPLC/MS analysis for the transglucosylated steviol glycosides prepared using the crude enzyme liquid of the Lactobacillus mali strain. It was confirmed through FIGS. 10 to 16 that in the transglucosylated steviol glycosides prepared using the crude enzyme liquid of the Lactobacillus mali strain, 1 to 4 glucose molecules were transferred to the steviol glycosides (stevioside, Rebaudiosides A/C/E/F, Rubusoside, and Dulcoside A).

Example 3: Effect of Temperature on Synthesis of Transglucosylated Steviol Glycoside In the production of the transglucosylated steviol glycosides by the crude enzyme liquids derived from the Lactobacillus mali strain, the effect of temperature was evaluated. Steviol glycosides (stevioside and Rebaudioside A) and sugar were dissolved in a 0.05 M acetic acid buffer solution (pH 5.0), and the crude enzyme liquids were added thereto, followed by contacting at 10° C. to 80° C. for 24 hours. After the reaction, the amount of the transglucosylated steviol glycosides in the reaction solutions was analyzed by HPLC.

FIG. 17 is graphs showing the conversion rate of the transglucosylated steviol glycosides (Stevioside and Rebaudioside A) according to temperature. Based on FIG. 17, the conversion rate to the transglucosylated steviol glycosides by the crude enzyme liquids of the Lactobacillus ma/i strain was as high as 10% to 70% at 10° C. to 50° C.

Example 4: Effect of pH on Synthesis of Transglucosylated Steviol Glycoside

In the production of the transglucosylated steviol glycosides by the crude enzyme liquids of the Lactobacillus mali strain, the effect of pH was evaluated. Steviol glycosides and sugar were dissolved in a 0.05 M acetic acid buffer solution (pH 2.0 to pH 5.0), a phosphate buffer solution (pH 6.0), a Tris buffer solution (pH 7.0 to pH 8.0), and sodium bicarbonate buffer solution (pH 9.0). Thereafter, the crude enzyme liquids were added thereto, and the reaction was carried out at pH 2 to pH 9 for 24 hours. After the reaction, the amount of the transglucosylated steviol glycosides was analyzed by HPLC.

FIG. 18 is graphs showing the synthetic conversion rate of the transglucosylated steviol glycoside according to pH. Based on FIG. 18, the conversion rate to the transglucosylated steviol glycosides by the crude enzyme liquids of the Lactobacillus mali strain was high at pH 4.0 to pH 7.0, and particularly, showed the highest conversion rate of 90% at pH 5.0.

Example 5: Analysis of Transglucosylated Steviol Glycoside According to Concentration of Steviol Glycoside The production of the transglucosylated steviol glycosides according to the concentrations of the steviol glycosides by the crude enzyme liquids of Lactobacillus mali was evaluated. Sugar and steviol glycosides (stevioside and Rebaudioside A) were dissolved in an acetic acid buffer solution (pH 5.0), and the reaction was carried out at 40° C. for 24 hours. After the reaction, the production of the transglucosylated steviol glycosides was analyzed by HPLC.

FIG. 18 is graphs showing the conversion rate of the transglucosylated steviol glycosides according to the concentrations of the steviol glycosides. As a result, it was confirmed that the conversion rate to the transgucosylated steviol glycosides by the crude enzyme liquids of Lactobacillus mali was high at 0% (w/w) to 4% (w/w), and particularly, was the highest at 6% (w/w).

FIG. 18 showed the synthetic conversion rate of transglucosylated Rebaudioside A according to the concentrations of Rebaudioside A. As a result, it was confirmed that the conversion rate to transglucosylated Rebaudioside A by the crude enzyme liquids of *Lactobacillus mali* was high at 0% (w/w) to 32% (w/w), and particularly, was the highest at 6% (w/w).

Example 6: Nuclear Magnetic Resonance (NMR) Analysis of Transglucosylated Steviol Glycoside Sugar and steviol glycosides were dissolved in an acetic acid buffer solution (pH 5.0), and then the crude enzyme liquids were added thereto, followed by contacting at 40° C. for 24 hours. The reaction solutions were inactivated at 100° C., and then impurities were removed using a 0.45 µm filter. Each of the steviol glycosides (Stevioside and Rebaudioside A), in which one glucose was transferred, was purely separated using an HP20 resin. The bonding structures of the separated transglucosylated Stevioside and transglucosylated Rebaudioside A were analyzed by $^1H/^{13}C$ NMR, homonuclear correlation spectroscopy (COSY), total correlation spectroscopy (TOCSY), heteronuclear single-quantum coherence (HSQC), and heteronuclear multiple-bond correlation (HMBC). In addition, the results thereof ($^1H/^{13}C$ NMR, COSY, and HMBC) are shown in Tables 1 and 2.

Additionally, as a result of identifying the structures of the transglucosylated Stevioside and transglucosylated Rebaudioside A, it was confirmed that these were novel compounds as the transglucosylated Stevioside is 13-[(2-O-β-D-glucopyranosyl-β-D-glucopyranosyl)oxy]ent-kaur-16-en-19-oic acid 6-O-α-D-glucopyranosyl-β-D-glucopyranosyl ester and the transglucosylated Rebaudioside A is 13-[(2-O-β-D-glucopyranosyl-3-O-β-D-glucopyranosyl-β-D-glucopyranosyl)oxy]ent-kaur-16-en-19-oic acid 6-O-α-D-glucopyranose-β-D-glucopyranosyl ester.

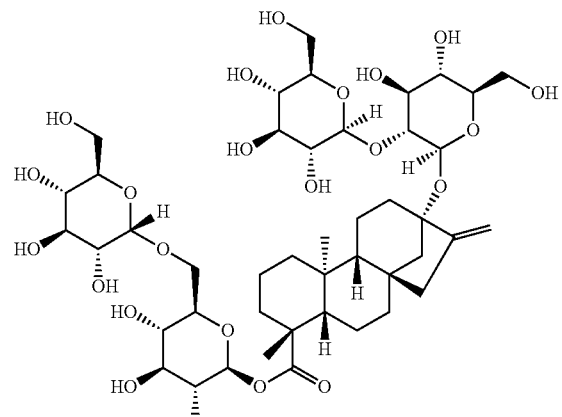

<Diagram of transglucosylated Stevioside>

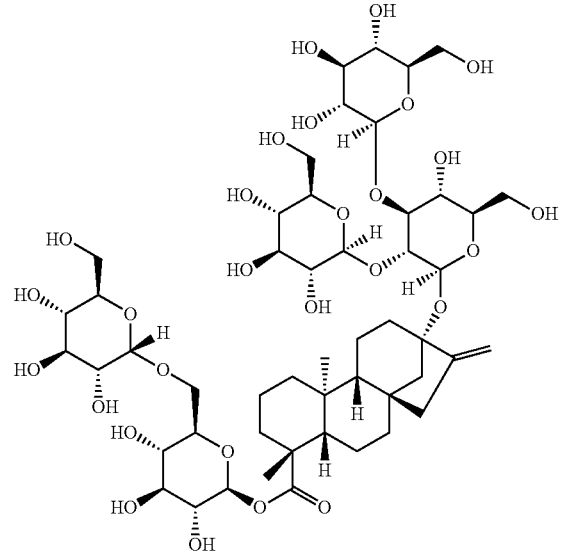

<Diagram of transglucosylated Rebaudioside A>

TABLE 1

| No. | $\delta_H$ mult. (J in Hz) | $\delta_C$ | mult. | HMBC Correlation | COSY corr. | Key ROESY corr. |
|---|---|---|---|---|---|---|
| 1 | 0.76 br m | 40.3 | $CH_2$ | | $1.37^w$, 1.78, 1.81 | |
| | 1.81 br m | | | | 0.76, 1.36 | |
| 2 | 1.36 br m | 18.6 | $CH_2$ | | 1.78, 1.81 | |
| | 1.78 br m | | | | 1.36 | |
| 3 | 0.99 br t (10.5) | 37.5 | $CH_2$ | 40.3, 43.7, 56.9, 56.9 | 1.78, 2.08 | |
| | 2.08 br d (10.5) | | | | 0.99 | |
| 4 | | 43.7 | C | | | |
| 5 | 1.05 br m | 56.9 | CH | 14.9, 21.3, 27.9, 39.6, 40.8, 43.7, 178.4 | 1.81 | |
| 6 | 1.81 br m | 21.3 | $CH_2$ | | 1.34 | 3.41 |
| 7 | 1.34 br m | 40.8 | $CH_2$ | 41.8, 53.5, 56.9 | 1.53 | |
| | 1.53 br m | | | | 1.34 | |
| 8 | | 41.8 | C | | | |
| 9 | 0.89 br d (5.5) | 53.5 | CH | 14.9, 20.3, 36.0, 39.6, 41.8, 44.1, 46.9 | 1.54 | |
| 10 | | 39.6 | C | | | |
| 11 | 1.54 br m | 20.3 | $CH_2$ | 41.8, 86.8 | 1.75, 1.89 | |
| | 1.75 br d (10.5) | | | | 1.54, $1.89^w$ | |
| 12 | 1.46 br m | 36.0 | $CH_2$ | | 1.54, 1.89 | |
| | 1.89 br m | | | | 1.46, 1.54, 1.75 | |
| 13 | | 86.8 | C | | | |

TABLE 1-continued

| No. | $\delta_H$ mult. (J in Hz) | $\delta_C$ | mult. | HMBC Correlation | COSY corr. | Key ROESY corr. |
|---|---|---|---|---|---|---|
| 14 | 1.40 br d (10.5) | 44.1 | CH$_2$ | 36.0, 41.8, 53.5, 86.8 | 2.12 | |
| | 2.12 br m | | | 46.9, 86.8 | 1.40, 1.94 | |
| 15 | 1.94 br d (16.0) | 46.9 | CH$_2$ | 44.1, 53.5, 86.8 | 2.13 | |
| | 2.13 br d (16.0) | | | 53.5, 152.9 | 1.94, 2.12 | |
| 16 | | 152.9 | C | | | |
| 17 | 4.84 br s | 104.9 | CH$_2$ | 46.9, 86.8, 152.9 | 2.13 | |
| | 5.09 br s | | | 46.9, 86.8, 152.9 | 2.13, 1.94 | |
| 18 | 1.17 s | 27.9 | CH$_3$ | 37.5, 43.7, 56.9, 178.4 | | 3.23, 3.25, 3.41, 3.58, 3.63 |
| 19 | | 178.4 | C | | | |
| 20 | 0.83 s | 14.9 | CH$_3$ | 39.6, 40.3, 53.5, 56.9 | | 3.23, 3.25, 3.41, 3.63 |
| 1' | 5.35 d (8.0) | 94.1 | CH | 75.5, 178.4 | 3.41 | 3.41, 3.46, 3.66 |
| 2' | 3.41 br m | 71.8 | CH | 76.3, 94.1 | 3.46, 5.35 | |
| 3' | 3.46 br m | 76.3 | CH | 68.9, 71.8 | 3.41, 3.48 | |
| 4' | 3.48 br m | 68.9 | CH | 65.1, 75.2, 76.3 | 3.46, 3.66 | |
| 5' | 3.66 br m | 75.2 | CH | | 3.48, 3.64 | |
| 6' | 3.64 br m | 65.1 | CH$_2$ | 97.7 | 3.87 | |
| | 3.87 br d (10.0) | | | 97.7 | 3.64 | |
| 1" | 4.64 br d (7.5) | 95.8 | CH | 76.0, 86.8 | 3.46 | 3.26, 3.46, 3.58 |
| 2" | 3.46 br m | 80.5 | CH | 76.2, 95.8, 103.1 | 4.64, 3.58 | |
| 3" | 3.58 br m | 76.2 | CH | 69.4, 80.5, 95.8 | 3.33, 3.46 | 3.26 |
| 4" | 3.33 br m | 69.4 | CH | | 3.26, 3.58 | |
| 5" | 3.26 br m | 75.6 | CH | | 3.33, 3.62 | 3.58 |
| 6" | 3.62 br m | 60.6 | CH$_2$ | 69.4 | 3.26, 3.76 | |
| | 3.76 br d (11.5) | | | | 3.62 | |
| 1''' | 4.62 d (8.0) | 103.1 | CH | 76.0, 80.5 | 3.23 | 3.23, 3.32, 3.41, 3.46 |
| 2''' | 3.23 t (8.0) | 74.2 | CH | 75.7, 103.1 | 3.41, 4.62 | |
| 3''' | 3.41 br m | 75.7 | CH | | 3.23, 3.25 | |
| 4''' | 3.25 br m | 69.7 | CH | 61.1, 75.7, 76.3 | 3.32, 3.41 | |
| 5''' | 3.32 br m | 76.3 | CH | 61.1, 69.7 | 3.25, 3.58 | |
| 6''' | 3.58 br m* | 61.1 | CH$_2$ | 76.3 | 3.32, 3.78 | |
| | 3.78 br d (11.5) | | | 69.7, 76.3 | 3.58 | |
| 1'''' | 4.83 br d (3.5) | 97.7 | CH | 65.1, 71.7, 73.1 | 3.45 | 3.45, 3.64 |
| 2'''' | 3.45 br m | 71.4 | CH | 73.1 | 3.63, 4.83 | |
| 3'''' | 3.63 br t (9.0) | 73.1 | CH | 69.3, 71.4 | 3.34, 3.45 | |
| 4'''' | 3.34 t (9.0) | 69.3 | CH | 60.3, 71.7, 73.1 | 3.58, 3.63 | |
| 5'''' | 3.58 br m | 71.7 | CH | | 3.34, 3.67 | |
| 6'''' | 3.67 br m* | 60.3 | CH$_2$ | 71.7, 69.3 | 3.58, 3.71 | |
| | 3.71 br d (11.5) | | | | 3.67 | |

TABLE 2

| No. | $\delta_H$ mult. (J in Hz) | $\delta_C$ | mult | HMBC Correlation | COSY corr. | Key ROESY corr. |
|---|---|---|---|---|---|---|
| 1 | 0.76 br m | 40.3 | CH$_2$ | 15.0 | 1.37$^w$, 1.78, 1.81 | |
| | 1.81 br m | | | | 1.37 | |
| 2 | 1.37 br m | 18.7 | CH$_2$ | | 1.78 | |
| | 1.78 br m | | | | 1.37 | |
| 3 | 0.99 br m | 37.6 | CH$_2$ | 40.3, 56.9 | 1.78, 2.08 | |
| | 2.08 br m | | | | 0.99 | |
| 4 | | 43.8 | C | | | |
| 5 | 1.05 br m | 56.9 | CH | 15.0, 21.4, 28.0, 39.3, 40.9, 43.8, 178.4 | 1.81 | |
| 6 | 1.81 br m | 21.4 | CH$_2$ | | 1.35 | 3.40 |
| 7 | 1.35 br m | 40.9 | CH$_2$ | 56.9 | 1.53 | |
| | 1.53 br m | | | | 1.35, 1.81$^w$ | |
| 8 | | 42.0 | C | | | |
| 9 | 0.89 br s | 53.5 | CH | 15.0, 20.3, 36.3, 39.3, 42.0, 44.0, 47.1 | 1.54 | |
| 10 | | 39.3 | C | | | |
| 11 | 1.54 br m | 20.3 | CH$_2$ | 42.0, 53.5, 87.1 | 1.75, 1.89 | |
| | 1.75 br m | | | 87.3 | 1.54, 1.89$^w$ | |
| 12 | 1.46 br m | 36.3 | CH$_2$ | | 1.89 | |
| | 1.89 br m | | | | 1.46, 1.75 | |
| 13 | | 87.1 | C | | | |
| 14 | 1.43 br m | 44.0 | | 36.3, 42.0, 53.5, 87.1, 47.1, 87.1, 152.9 | 2.09 | |
| | 2.09 br m | | | | 1.43 | |
| 15 | 1.95 br d (16.0) | 47.1 | CH$_2$ | 44.0 | 2.14 | |
| | 2.14 br d (16.0) | | | 53.5, 152.9 | 1.95, 2.09 | |
| 16 | | 152.9 | C | | | |
| 17 | 4.85 br s | 104.8 | CH$_2$ | 47.1, 87.1, 152.9 | 2.14 | |
| | 5.08 br s | | | 47.1, 87.1, 152.9 | 2.14, 1.95 | |
| 18 | 1.17 s | 28.0 | CH$_3$ | 37.6, 43.8, 56.9, 178.4 | | 1.81, 3.40 |

TABLE 2-continued

| No. | $\delta_H$ mult. (J in Hz) | $\delta_C$ | mult | HMBC Correlation | COSY corr. | Key ROESY corr. |
|---|---|---|---|---|---|---|
| 19 | | 178.4 | C | | | |
| 20 | 0.83 s | 15.0 | CH$_3$ | 39.3, 40.3, 53.5, 56.9 | | 3.17, 3.41, 5.37 |
| 1' | 5.37 d (8.0) | 94.1 | CH | 75.2, 178.4 | 3.40 | 3.40, 3.47, 3.66 |
| 2' | 3.40 br m | 71.9 | CH | 76.3, 94.1 | 3.47, 5.37 | 1.17, 1.81 |
| 3' | 3.47 br m | 76.3 | CH | 68.9, 71.9, | 3.40 | |
| 4' | 3.48 br m | 68.9 | CH | 65.2, 75.2, 76.3 | 3.66 | |
| 5' | 3.66 br m | 75.2 | CH | | 3.48, 3.64 | |
| 6' | 3.64 br m | 65.2 | CH$_2$ | 97.8 | 3.87 | |
|    | 3.87 br m* | | | 97.8 | 3.64 | 4.83 |
| 1" | 4.66 ovlp solv. | 95.9 | CH | 75.2, 87.1 | 3.65 | |
| 2" | 3.65 br m | 78.6 | CH | 85.1, 95.9, 102.11 | 4.66 | |
| 3" | 3.80 br m | 85.1 | CH | 68.5, 78.6, 102.20 | 3.42 | 3.30, 3.70, |
| 4" | 3.42 br m | 68.5 | CH | 60.8, 75.2, 85.1 | 3.29~3.33, 3.80 | |
| 5" | 3.30 br m | 75.2 | CH | | 3.64 | 3.80 |
| 6" | 3.64 br m | 60.8 | CH$_2$ | | 3.30, 3.78 | |
|    | 3.78 br m | | | | 3.64 | |
| 1''' | 4.77 br d (8.0) | 102.1 | CH | 75.9, 76.5, 78.6 | 3.17 | 3.31, 3.37, 3.65 |
| 2''' | 3.17 br m | 74.1 | CH | 75.9, 120.1 | 3.37, 4.77 | 1.46, 2.09 |
| 3''' | 3.37 br m | 75.9 | CH | 70.2, 74.1 | 3.17 | |
| 4''' | 3.18 br m | 70.3 | CH | 61.5, 75.9, 76.5 | 3.31 | |
| 5''' | 3.31 br m | 76.5 | CH | 61.5 | 3.18, 3.55 | |
| 6''' | 3.55 br m* | 61.5 | CH$_2$ | 76.5 | 3.80 | |
|    | 3.80 br m* | | | | 3.55 | |
| 1'''' | 4.70 ovlp solv. | 102.2 | CH | 75.8, 76.1, 85.1, | 3.29 | |
| 2'''' | 3.29 br m | 73.3 | CH | 75.8, 102.2 | 3.42, 4.70 | |
| 3'''' | 3.42 br m | 75.8 | CH | 69.5, 73.3 | 3.29~3.33 | |
| 4'''' | 3.33 br m | 69.5 | CH | 61.6, 75.8, 76.1 | 3.42 | |
| 5'''' | 3.41 br m | 76.1 | CH | | 3.63 | |
| 6'''' | 3.63 br m | 60.6 | CH$_2$ | 76.3 | 3.41, 3.83 | |
|    | 3.83 br d (12.0) | | | 69.5 | 3.63 | |
| 1''''' | 4.83 br d (3.0) | 97.8 | CH | 65.2, 71.7, 73.1 | 3.45 | 3.45, 3.64 |
| 2''''' | 3.45 br m | 71.4 | CH | 97.8, | 3.63, 4.83 | |
| 3''''' | 3.63 br m | 73.1 | CH | 69.3, 71.4 | 3.34, 3.45 | |
| 4''''' | 3.34 br m | 69.3 | CH | 60.3, 71.7, 73.1 | 3.59, 3.63 | |
| 5''''' | 3.59 br m | 71.7 | CH | 3.34, 3.68 | | |
| 6''''' | 3.68 br m* | 60.3 | CH$_2$ | 71.7, 69.3 | 3.59, 3.71 | |
|    | 3.71 br d (12.0) | | | | 3.68 | |

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A method for preparing a transglucosylated steviol glycoside, comprising:
   (a) obtaining a solution comprising at least one steviol glycoside and sugar dissolved in a buffer,
   (b) reacting at least one of a culture of *Lactobacillus mali* microorganism and a supernatant thereof, with the solution of step (a) to provide a transglucosylated steviol glycoside;
   wherein the steviol glycoside is selected from the group consisting of Stevioside, Rubusoside, Dulcoside A, Rebaudioside A, Rebaudioside B, Rebaudioside C, Rebaudioside D, Rebaudioside E, Rebaudioside F, and Rebaudioside M; and
   the transglucosylated steviol glylcoside comprises a glucose molecule linked via an α-(1,6) bond to the glucose molecule linked to the 19-OH site of the steviol glycoside.

2. The method according to claim 1, wherein step (b) is carried out at a pH of 3 to 8 at a temperature of 10° C. to 60° C.

3. The method according to claim 1, wherein the transglucosylated steviol glycoside comprises 1 to 4 glucose molecules.

4. The method according to claim 1, wherein the method further comprises centrifuging the media of the culture of *Lactobacillus mali* and collecting the supernatant, and wherein step (b) comprises reacting the supernatant with the solution of step (a) to provide the transglucosylated steviol glycoside.

* * * * *